(12) United States Patent
Pulé et al.

(10) Patent No.: US 11,242,377 B2
(45) Date of Patent: Feb. 8, 2022

(54) CHIMERIC RECEPTOR WITH LIGAND BINDING EXODOMAIN AND CYTOKINE AND T CELL SIGNALLING ENDODOMAINS

(71) Applicant: AUTOLUS LIMITED, London (GB)

(72) Inventors: Martin Pulé, London (GB); Shaun Cordoba, London (GB); Matteo Righi, London (GB)

(73) Assignee: AUTOLUS LIMITED, London (GB)

( * ) Notice: Subject to any disclaimer, the term of this patent is extended or adjusted under 35 U.S.C. 154(b) by 606 days.

(21) Appl. No.: 15/770,110

(22) PCT Filed: Oct. 21, 2016

(86) PCT No.: PCT/GB2016/053290
§ 371 (c)(1),
(2) Date: Apr. 20, 2018

(87) PCT Pub. No.: WO2017/068360
PCT Pub. Date: Apr. 27, 2017

(65) Prior Publication Data
US 2018/0312570 A1    Nov. 1, 2018

(30) Foreign Application Priority Data

Oct. 23, 2015 (GB) .................................... 1518816

(51) Int. Cl.
C07K 14/715 (2006.01)
C07K 14/705 (2006.01)
(Continued)

(52) U.S. Cl.
CPC .. *C07K 14/70578* (2013.01); *C07K 14/70521* (2013.01); *C07K 14/7155* (2013.01); *C07K 16/2803* (2013.01); *C07K 16/30* (2013.01);
*C07K 19/00* (2013.01); *C12N 5/0638* (2013.01); *A61K 35/17* (2013.01);
(Continued)

(58) Field of Classification Search
CPC ............ C07K 14/715; C07K 14/71555; C07K 19/00; C07K 16/46; C07K 14/7051; C07K 14/70517; C07K 14/70578; C07K 14/70507
See application file for complete search history.

(56) References Cited

U.S. PATENT DOCUMENTS

2018/0244797 A1   8/2018  Pule et al.

FOREIGN PATENT DOCUMENTS

WO     WO-99/57268 A1     11/1999
WO     WO-2008/095141 A2   8/2008
(Continued)

OTHER PUBLICATIONS

Huang et al. (2015, PLOS One, 10(7), e0133152, pp. 1-18) (cited in IDS of Aug. 30, 2018) (Year: 2015).*
(Continued)

*Primary Examiner* — Zachary C Howard
(74) *Attorney, Agent, or Firm* — Marshall, Gerstein & Borun LLP

(57) ABSTRACT

The present invention provides a chimeric receptor which comprises: a ligand-binding exodomain; and an endodomain which comprises: (i) a cytokine receptor endodomain; and (ii) an intracellular T cell signalling domain.

35 Claims, 10 Drawing Sheets

Specification includes a Sequence Listing.

(51) Int. Cl.
| | |
|---|---|
| C07K 19/00 | (2006.01) |
| C07K 16/30 | (2006.01) |
| C12N 5/0783 | (2010.01) |
| C07K 16/28 | (2006.01) |
| C07K 14/725 | (2006.01) |
| A61K 39/00 | (2006.01) |
| A61K 35/17 | (2015.01) |

(52) U.S. Cl.
CPC ............... A61K 2039/5156 (2013.01); A61K 2039/5158 (2013.01); A61K 2039/54 (2013.01); A61K 2039/572 (2013.01); C07K 14/7051 (2013.01); C07K 2317/622 (2013.01); C07K 2319/03 (2013.01); C07K 2319/30 (2013.01); C07K 2319/72 (2013.01); C07K 2319/74 (2013.01); C12N 2510/00 (2013.01)

(56) References Cited

FOREIGN PATENT DOCUMENTS

| WO | 2012/033885 A1 † | 3/2012 |
|---|---|---|
| WO | 2012/138858 A1 † | 10/2012 |
| WO | WO-2012/138858 A1 | 10/2012 |
| WO | WO-2013/074916 A1 | 5/2013 |
| WO | WO-2014/100385 A1 | 6/2014 |
| WO | 2014/124143 A1 † | 8/2014 |
| WO | WO-2014/152177 A1 | 9/2014 |
| WO | 2016/014565 A2 † | 1/2016 |
| WO | 2016/014576 A1 † | 1/2016 |
| WO | 2016/127257 A1 † | 8/2016 |
| WO | WO-2016/134284 A1 | 8/2016 |
| WO | 2016/172606 A1 † | 10/2016 |
| WO | 2016/197108 A1 † | 12/2016 |
| WO | WO-2017/029512 A1 | 2/2017 |

OTHER PUBLICATIONS

Carrette et al, 2012, Semin Immuno. 24(3): 209-217.*
Jayaraman et al, 2020. EBioMedicine. 58: 102931; pp. 1-12 as printed.*
Ngo et al., "Ex vivo gene transfer for improved adoptive immunotherapy of cancer," Human Molecular Genetics 20(1):R93-R99 (2011).
Abate-Daga et al., A novel chimeric antigen receptor against prostate stem cell antigen mediates tumor destruction in a humanized mouse model of pancreatic cancer, Hum. Gene. Ther. 25:1003-1012 (2014).
Baker et al., Hematopoietic cytokine receptor signaling, Oncogene. 26:6724-6737 (2007).
Bridgeman et al., The optimal antigen response of chimeric antigen receptors harboring the CD3zeta transmembrane domain is dependent upon incorporation of the receptor into the endogenous TCR/CD3 complex, J Immunol. 184:6938-6949 (2010).
Chang et al., Five different anti-prostate-specific membrane antigen (PSMA) antibodies confirm PSMA expression in tumor-associated neovasculature, Cancer Res. 59:3192-3198 (1999).
Donelly et al., The 'cleavage' activities of foot-and-mouth disease virus 2A site-directed mutants and naturally occurring '2A-like' sequences, J. Gen. Virol. 82:1027-1041 (2001).
Hassuneh et al., Evidence for the participation of interleukin-2 (IL-2) and IL-4 in the regulation of autonomous growth and tumorigenesis of transformed cells of lymphoid origin, Blood. 89:610-620 (1997).
Hillerdal et al., Systemic treatment with CAR-engineered T cells against PSCA delays subcutaneous tumor growth and prolongs survival of mice, BMC Cancer. 14:30 (2014).
Huang et al., IGF1R- and ROR1-Specific CAR T Cells as a Potential Therapy for High Risk Sarcomas, PLOS ONE, 10:e0133152 (2015).
Hulme et al., Central Role for interleukin-2 in type 1 diabetes, Diabetes. 61:14-22 (2012).
International Preliminary Report on Patentability, PCT/GB2016/053290 (dated Apr. 24, 2018).
International Search Report and Written Opinion, PCT/GB2016/053290 (dated Feb. 3, 2017).
Morgenroth et al., Targeting of tumor cells expressing the prostate stem cell antigen (PSCA) using genetically engineered T-Cells, Prostate. 67:1121-1131 (2007).
Nagarkatti et al.,Constitutive activation of the interleukin 2 gene in the induction of spontaneous in vitro transformation and tumorigenicity of T Cells, Proc. Natl. Acad. Sci. 91:7638-7642 (1994).
Wilkie et al., Selective expansion of chimeric antigen receptor-targeted T-cells with potent effector function using interleukin-4, J Biol. Chem. 285:25538-25544 (2010).
Villarino et al., Mechanisms of Jak/STAT signaling in immunity and disease, J. Immunol., 194(1):21-7 (2015).
Koneru et al., IL-12 secreting tumor-targeted chimeric antigen receptor T cells eradicate ovarian tumors in vivo, Oncoimmunology, 4:3, e994446 (Mar. 2015).

\* cited by examiner
† cited by third party

FIGURE 5

>aCD22huLT22-CD8STK-IL2RB-2A-aCD22huRFB4-HNG-IL2RG-Zeta

<------------------------ huLT22 scFv ------------------------------------------
LPVTALLLPLALLLHAARPDIVMTQSPATLSVSPGERATLSCRSSQSLVHSNGNTYLHWYQQKPGQAPRLLIYKVSNRFSGVPARF

--------------------------- huLT22 scFv ----------------------------------------
SGSGSGAEFTLTISSLQSEDFAVYYCSQSTHVPWTFGQGTRLEIKRSGGGGSGGGGSGGGGSEVQLVESGAEVKKPGSSVKVSCKA

------------------------------- huLT22 scFv ------------------------------------
SGYTFTNYWINWVRQAPGQGLEWMGNIYPSDSFTNYNQKFKDRVTITADKSTSTVYLELRNLRSDDTAVYYCTRDTQERSWYFDVW

----------><--------------- CD8 STK ----------------------><--- TM -------------><-----
GQGTLVTVSDPTTTPAPRPPTPAPTIASQPLSLRPEACRPAAGGAVHTRGLDFACDIFWVVISVGSMGLIISLLCVYFWLERTMPR

------------------------------ dIL2RG ----------------------------------------><-----
IPTLKNLEDLVTEYHGNFSAWSGVSKGLAESLQPDYSERLCLVSEIPPKGGALGEGPGASPCNQHSPYWAPPCYTLKPETRRVKFS

-------------------------------------- CD3-Zeta --------------------------------------
RSADAPAYQQGQNQLYNELNLGRREEYDVLDKRRGRDPEMGGKPRRKNPQEGLYNELQKDKMAEAYSEIGMKGERRRGKGHDGLYQ -- CD3-Zeta --------><--- FMD-2A -------><--------- huRFB4 scFv ---------------------
GLSTATKDTYDALHMQALPPRRAEGRGSLLTCGDVEENPGPLPVTALLLPLALLLHAARPEVQLVESGGGLVQPGGSLRLSCAASG ------------------------------- huRFB4 scFv ------------------------------------
FAFSIYDMSWVRQVPGKGLEWVSYISSGGGTTYYPDTVKGRFTISRDNSRNTLDLQMNSLRVEDTAVYYCARHSGYGSSYGVLFAY ----------------------------------- huRFB4 scFv --------------------------------------
WGQGTLVTVSSGGGGSGGGGSGGGGSDIQMTQSPSSLSASVGDRVTITCRASQDISNYLNWLQQKPGKAPKLLIYYTSILHSGVPS ---------- huRFB4 scFv ------------------------><------- IgG1 Hinge ---------------><
RFSGSGSGTEFTLTISSLQPEDFATYYCQQGNTLPWTFGQGTKLEIKRSPAEPKSPDKTHTCPPCPKDPKACDIYIWAPLAGTCGL --- IgG1 Hinge ----->←--------------------- dIL2RB ---------------------------------
GHLLVGLSGAFGFIILVYLLINCRNTGPWLKKVLKCNTPDPSKFFSQLSSEHGGDVQKWLSSPFPSSSFSPGGLAPEISPLEVLER ----------------------------------- dIL2RB ------------------------------------------
DKVTQLLLQQDKVPEPASLSSNHSLTSCFTNQGYFFFHLPDALEIEACQVYFTYDPYSEEDPDEGVAGAPTGSSPQPLQPLSGEDD ---------------------------------- dIL2RB -------------------------------------------
AYCTFPSRDDLLLFSPSLLGGPSPPSTAPGGSGAGEERMPPSLQERVPRDWDPQPLGPPTPGVPDLVDFQPPPELVLREAGEEVPD -------------------- dIL2RB ------------------>
AGPREGVSFPWSRPPGQGEFRALNARLPLNTDAYLSLQELQGQDPTHL ☐ R11-il2b-z-2A-R12-il2g-z
■ R11-z-2A-R12-z

CHIMERIC RECEPTOR WITH LIGAND BINDING EXODOMAIN AND CYTOKINE AND T CELL SIGNALLING ENDODOMAINS

CROSS-REFERENCE TO RELATED APPLICATIONS

This application is the US national stage of International Patent Application No. PCT/GB2016/053290, filed 21 Oct. 2016, which claims priority benefit of Patent Application No. 1518816.2, filed 23 Oct. 2015 in the United Kingdom.

INCORPORATION BY REFERENCE OF MATERIAL SUBMITTED ELECTRONICALLY

This application includes and incorporates by reference the contents of a Sequence Listing, submitted to the U.S. Patent and Trademark Office as a text file named "52926_Seqlisting," which was created on Apr. 19, 2018, and which is 40,128 bytes in size.

FIELD OF THE INVENTION

The present invention relates to a chimeric receptor (CR), and a cell which expresses such a chimeric receptor.

BACKGROUND TO THE INVENTION

Chimeric Antigen Receptors (CARs)

A number of immunotherapeutic agents have been described for use in cancer treatment, including therapeutic monoclonal antibodies (mAbs), bi-specific T-cell engagers and chimeric antigen receptors (CARs).

Chimeric antigen receptors are proteins which graft the specificity of a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals.

The most common form of these molecules are fusions of single-chain variable fragments (scFv) derived from monoclonal antibodies which recognize a target antigen, fused via a spacer and a trans-membrane domain to a signaling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

There has been some success to date for the application of CAR T cells in the treatment of liquid tumours, such as leukemia and lymphoma. However, the use of CAR T cells for the treatment of solid tumours is more challenging, due to the immunosuppressive microenvironment which is hostile to T cells.

CAR T-cell persistence and activity can be enhanced by administration of cytokines, or by the CAR T-cells producing cytokines constitutively. However, these approaches have limitations: systemic administration of cytokines can be toxic; constitutive production of cytokines may lead to uncontrolled proliferation and transformation (Nagarkatti et al (1994) PNAS 91:7638-7642; Hassuneh et al (1997) Blood 89:610-620).

There is therefore a need for alternative CAR T-cell approaches, which facilitate engraftment and expansion of T cells, which are not associated with the disadvantages mentioned above.

The first CR has an endodomain which comprises a cytokine receptor endodomain (the common gamma chain) and an intracellular T cell signalling domain (CD3 zeta). The second CR has an endodomain which comprises a cytokine receptor endodomain (the IL2 receptor beta chain) and an intracellular T cell signalling domain (comprising both CD28 and OX40 co-stimulatory domains). The antigen-binding exodomains of the two chimeric receptors bind different epitopes on the same ligand. When the CRs bind the ligand, the cytokine endodomains on each molecule are brought into approximation, so that they can associate and lead to cytokine-like cell activation. Cell activation also occurs via the T-cell activating endodomains providing signal 1 and signal 2 to the cell. Note: Although only one chain is shown, the CRs in this system are homodimers.

Figure 3:
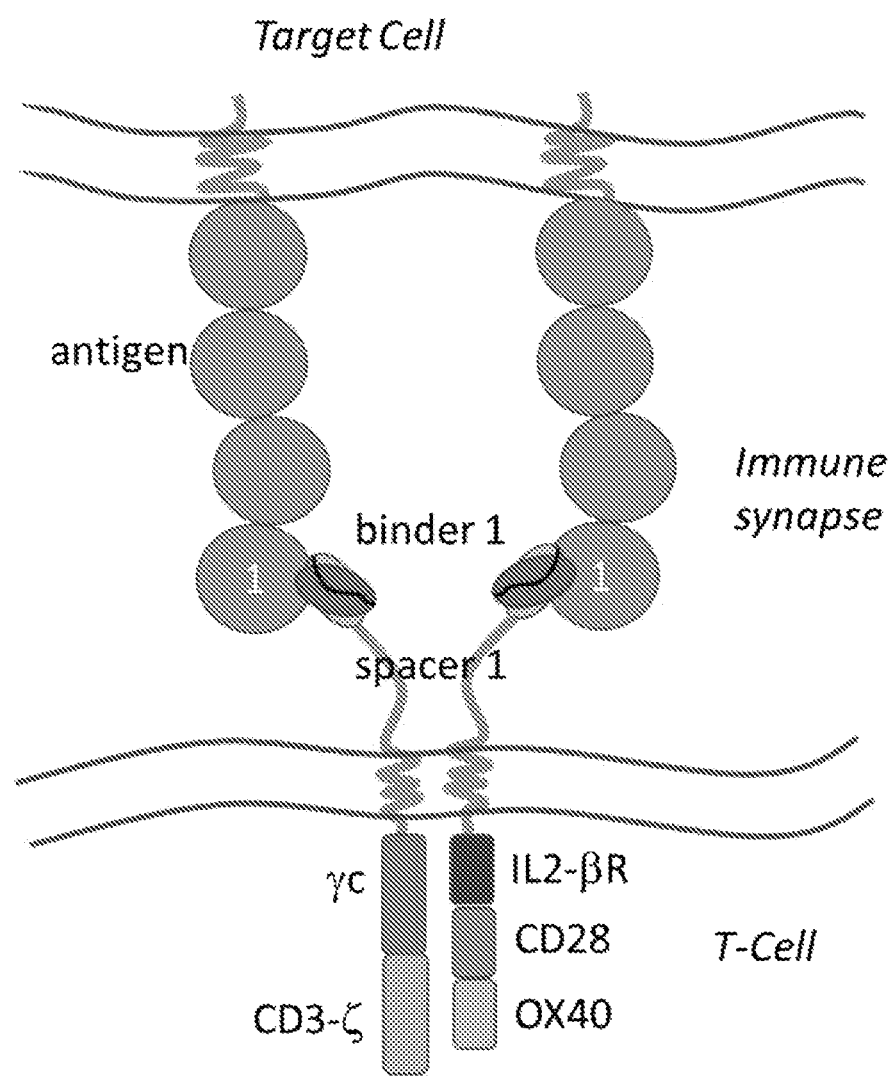

FIG. 3: Schematic Diagram of an Alternative Dual CR System of the Invention

Figure 1:
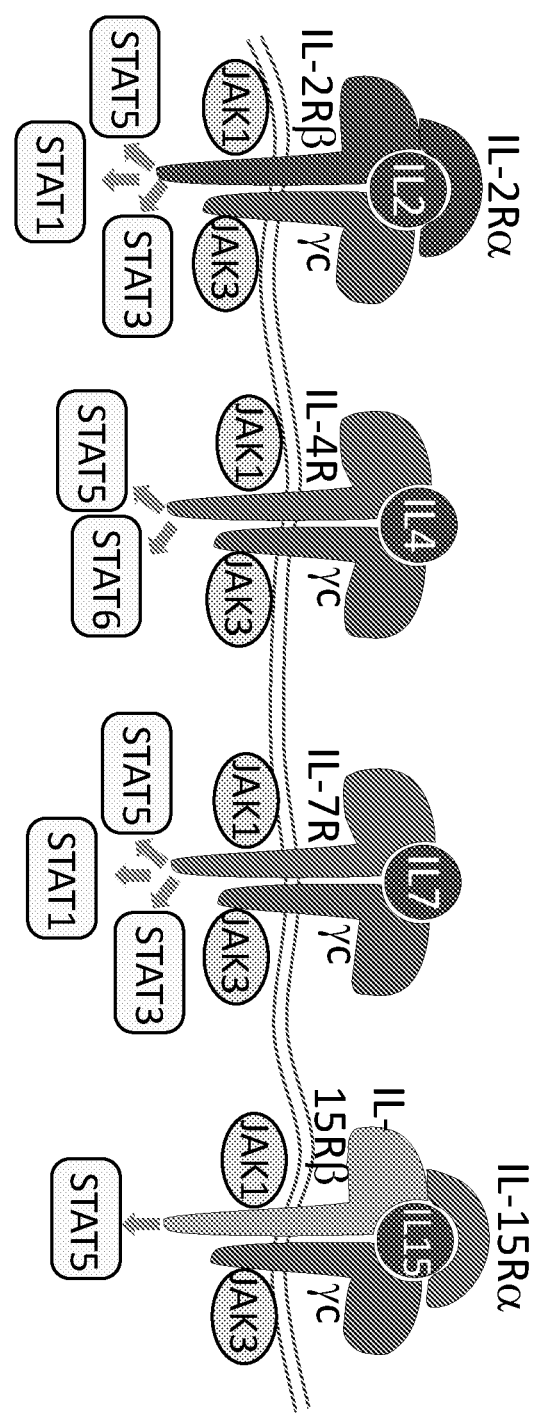
FIG. 1: Schematic diagram summarising the structure of various cytokine receptors, the cell types which produce the cytokines and the cell types which express the cytokine receptors.
Figure 2:
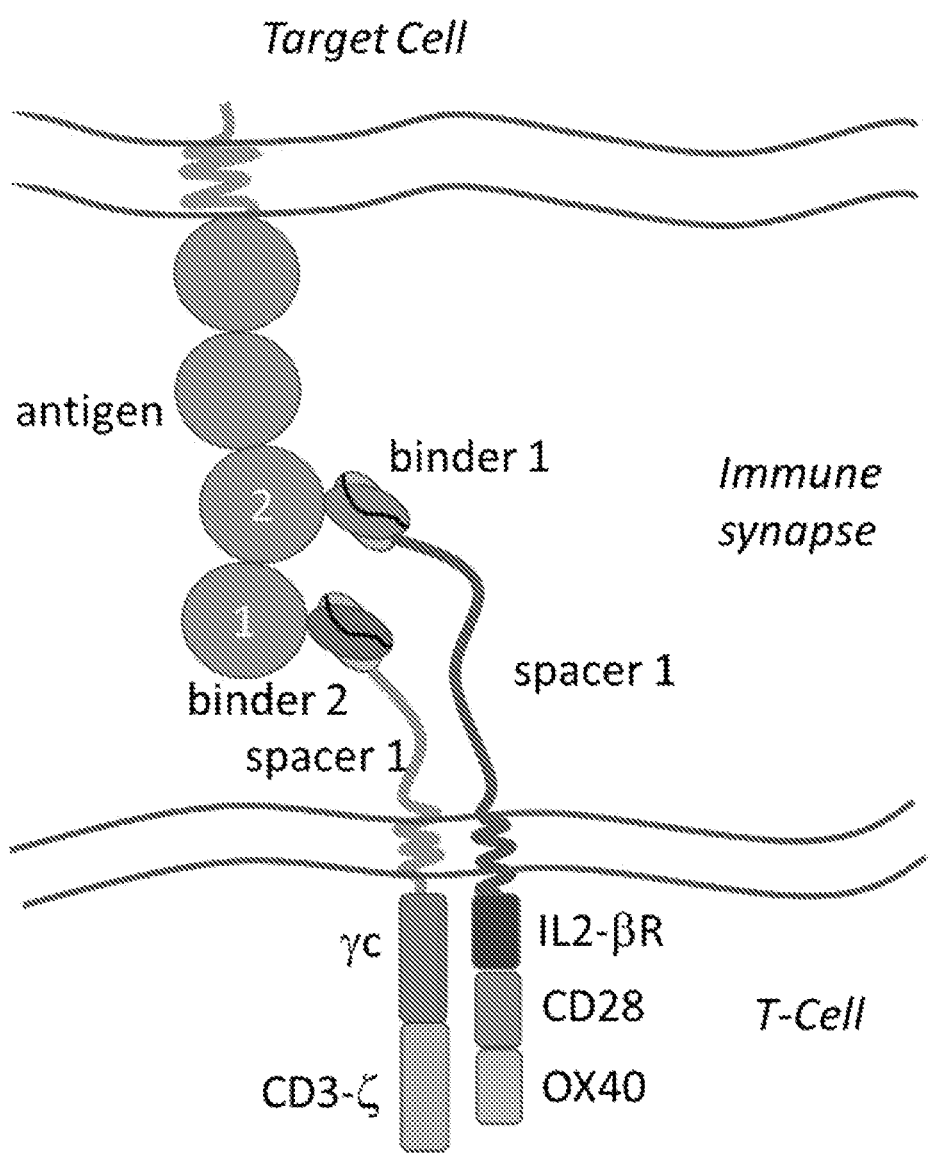
FIG. 2: Schematic Diagram of a Dual Chimeric Receptor System of the Invention

In this system, the first and second CRs have a similar structure to the ones shown in FIG. 2 in terms of endodomains etc. The difference is that the antigen-binding exodomains of the two chimeric receptors bind the same epitopes on the ligand. They may comprise identical antigen-binding portions. Where there is a tight synapse, the independent binding of an antigen by two chimeric receptors may bring the endodomains into close enough proximity for the cytokine endodomains to asscoiate, leading to activation. Note: Although only one chain is shown, the CRs in this system are homodimers.

Figure 4:
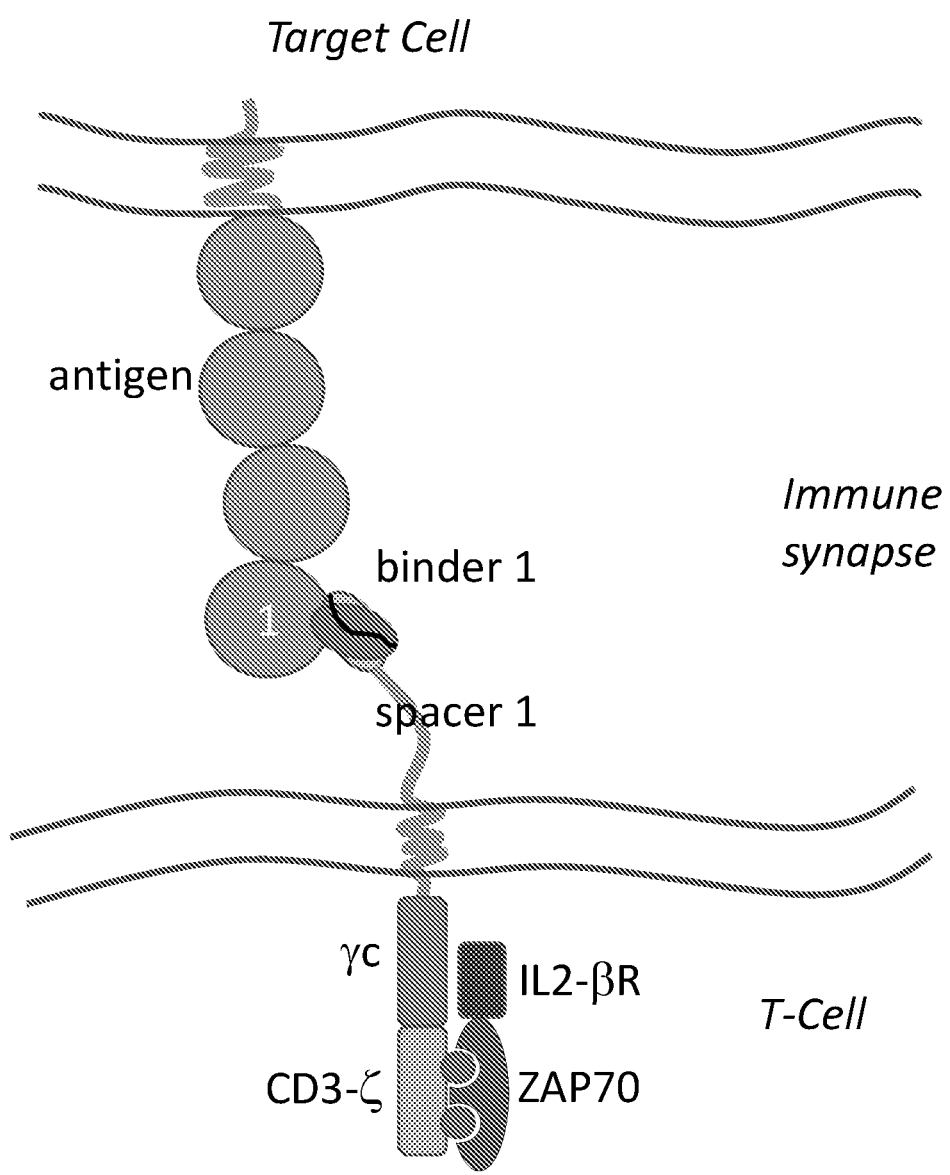

FIG. 4: Schematic Diagram of a CR:ZAP70 System of the Invention

In this system, a single CR recognizes the cognate antigen and its endodomain comprises not only of T-cell signalling (which at a minimum would contain the CD3-Zeta endodomain), but also a cytokine receptor endodomain (for instance either that from common gamma chain, or from the IL2 receptor beta chain). This receptor is co-expressed with a fusion between ZAP70 SH2 domain and a complimentary cytokine receptor endodomain (for instance if the CR contains the common gamma chain, the ZAP70 SH2 domain might be fused to the IL2 receptor beta chain). Upon recognition of antigen, the CR CD3-Zeta endodomain ITAMS become phosphorylated and recruit the ZAP70 fusion protein. Now the two endodomains of the cytokine receptor are closely approximated and a cytokine signal transmitted.

FIG. 5: Amino acid sequence (SEQ ID NO: 27) for a dual CR system as illustrated in FIG. 2, showing the individual components. In this construct, both CARs recognise CD22. The first CR comprises a binder based on LT22 and an endodomain which comprises the IL2 receptor beta chain; the second CR comprises a binder based on RFB4 and an endodomain which comprises the IL2 receptor gamma chain and CD3 zeta endodomain.

Figure 6:
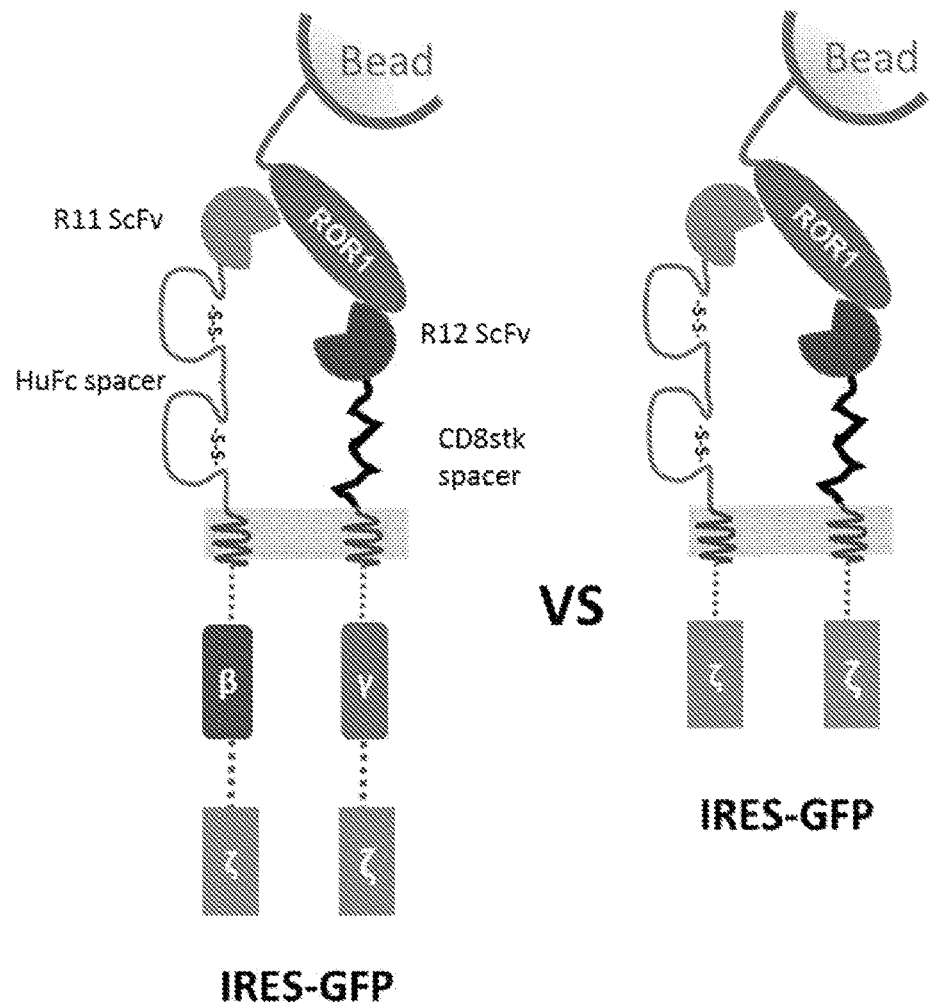

FIG. 6: Schematic diagram illustrating the chimeric receptor systems tested in the proliferation/survival assay described in Example 3. One chimeric receptor comprises an R11 scFv, whereas the other comprises an R12 scFv. R11 and R12 bind separate epitopes on the same antigen: ROR1.

Figure 7:
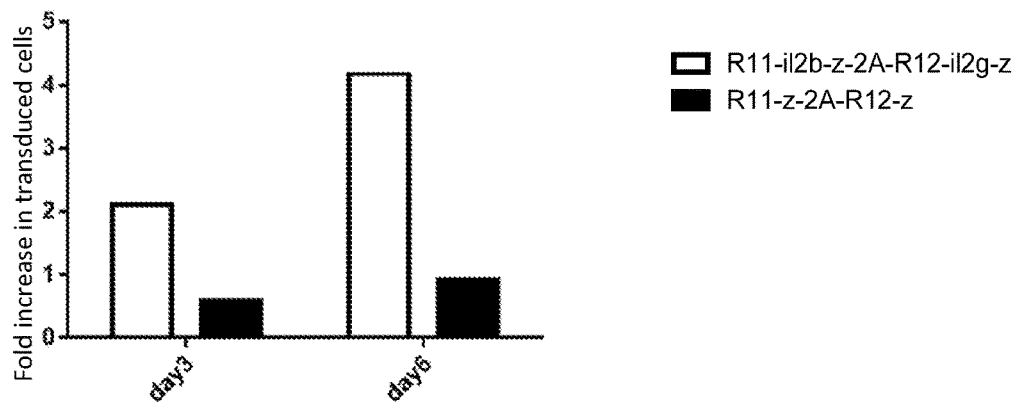

FIG. 7: Graph to show the fold increase of transduced cells when co-cultured with ligand-coated beads. R11-il2b-z-2A-R12-il2g-z is a construct encoding the 4th generation CAR system illustrated in FIG. 6, which comprises both cytokine receptor endodomains and CD3 zeta endodomains; R11-z-2A-R12-z is a construct encoding an equivalent chimeric receptor system which lacks the cytokine receptor endodomains.

Figure 8:
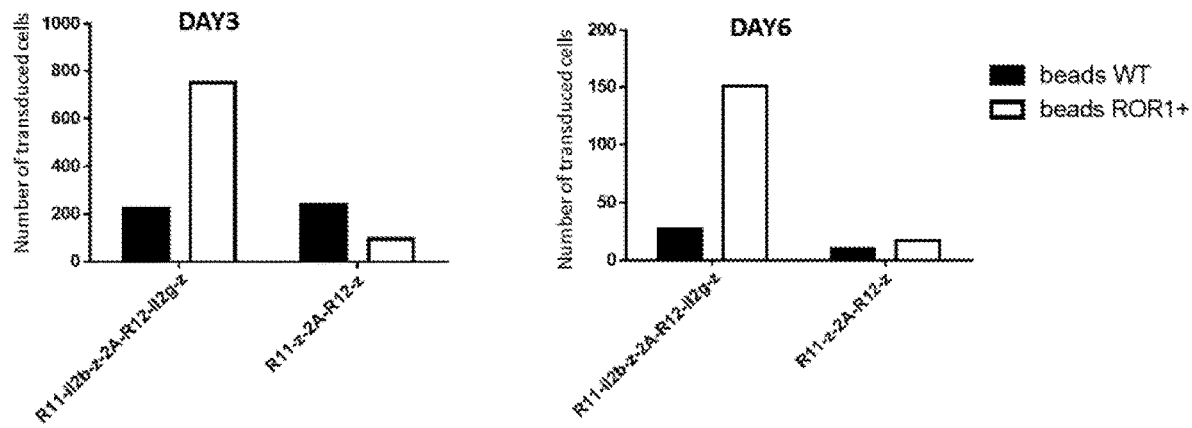

FIG. 8: Graph to show the number of transduced cells after co-culture with ROR1-coated beads after 3 and 6 days.

Figure 9:
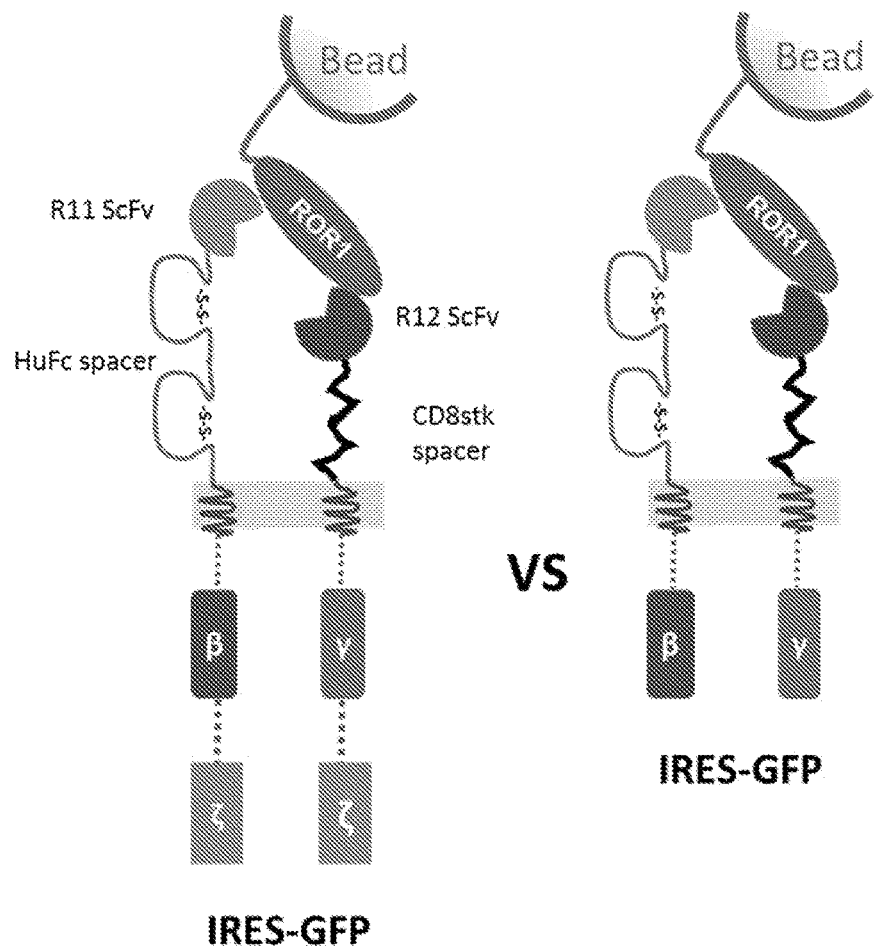

FIG. 9: Schematic diagram illustrating the chimeric receptor systems tested in the killing assay described in Example 4. One chimeric receptor comprises an R11 scFv, whereas the other comprises an R12 scFv. R11 and R12 bind separate epitopes on the same antigen: ROR1.

Figure 10:
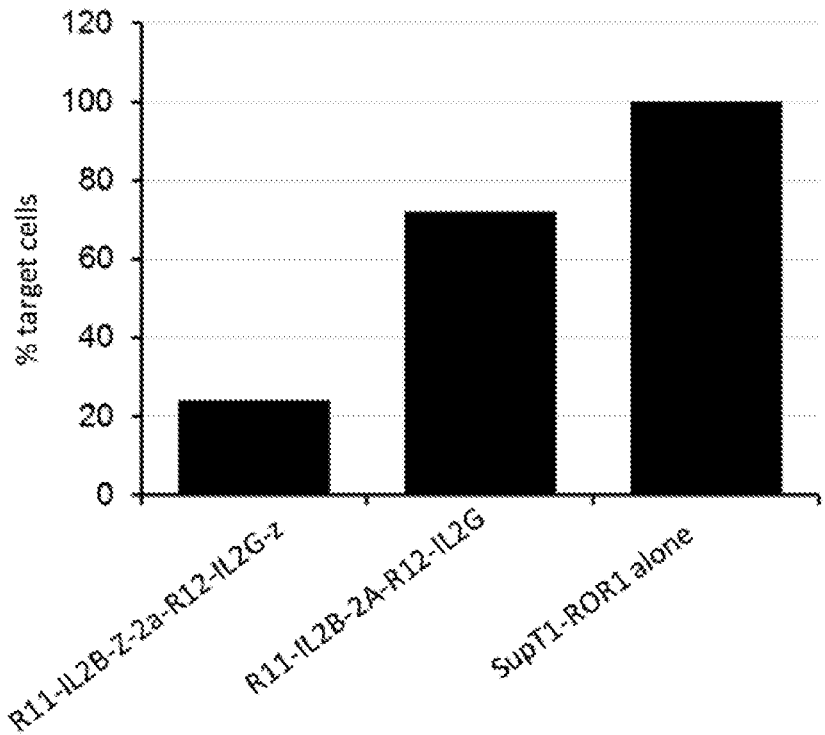

FIG. 10: Graph to show cell target cell killing after 48 hours incubation at a 10:1 E:T ratio. R11-IL2B-Z-2A-R12-IL2G-z is a construct encoding the 4th generation CAR system illustrated in FIG. 9, which comprises both cytokine receptor endodomains and CD3 zeta endodomains; R11-IL2B-2A-R12-IL2G is a construct encoding an equivalent chimeric receptor system which lacks the CD3 zeta endodomains.

Figure 11:
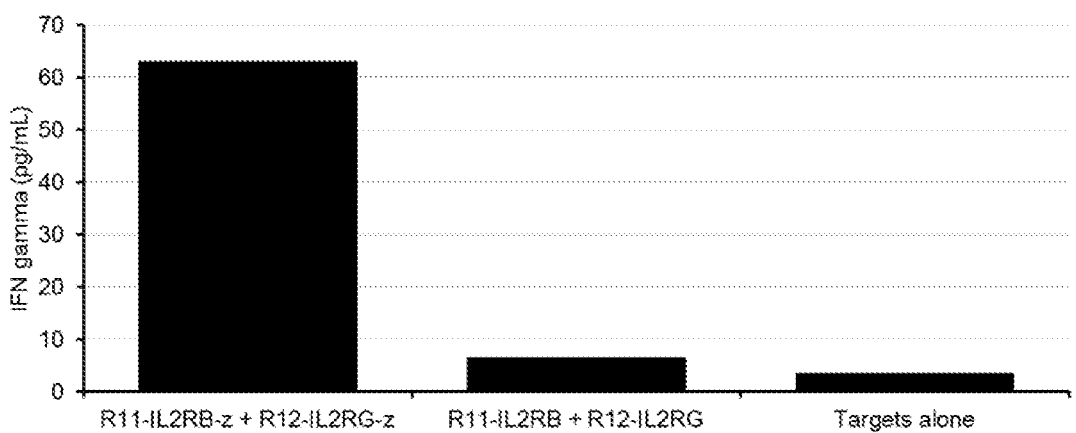

FIG. 11: Graph to show cell IFNγ secretion after 48 hours incubation at a 10:1 E:T ratio. R11-IL2RB-Z+R12-IL2RG-z denotes cells expressing the 4th generation CAR system illustrated in FIG. 9, which comprises both cytokine receptor endodomains and CD3 zeta endodomains; R11-IL2RB+R12-IL2RG denotes cells expressing an equivalent chimeric receptor system which lacks the CD3 zeta endodomains.

Figure 12:
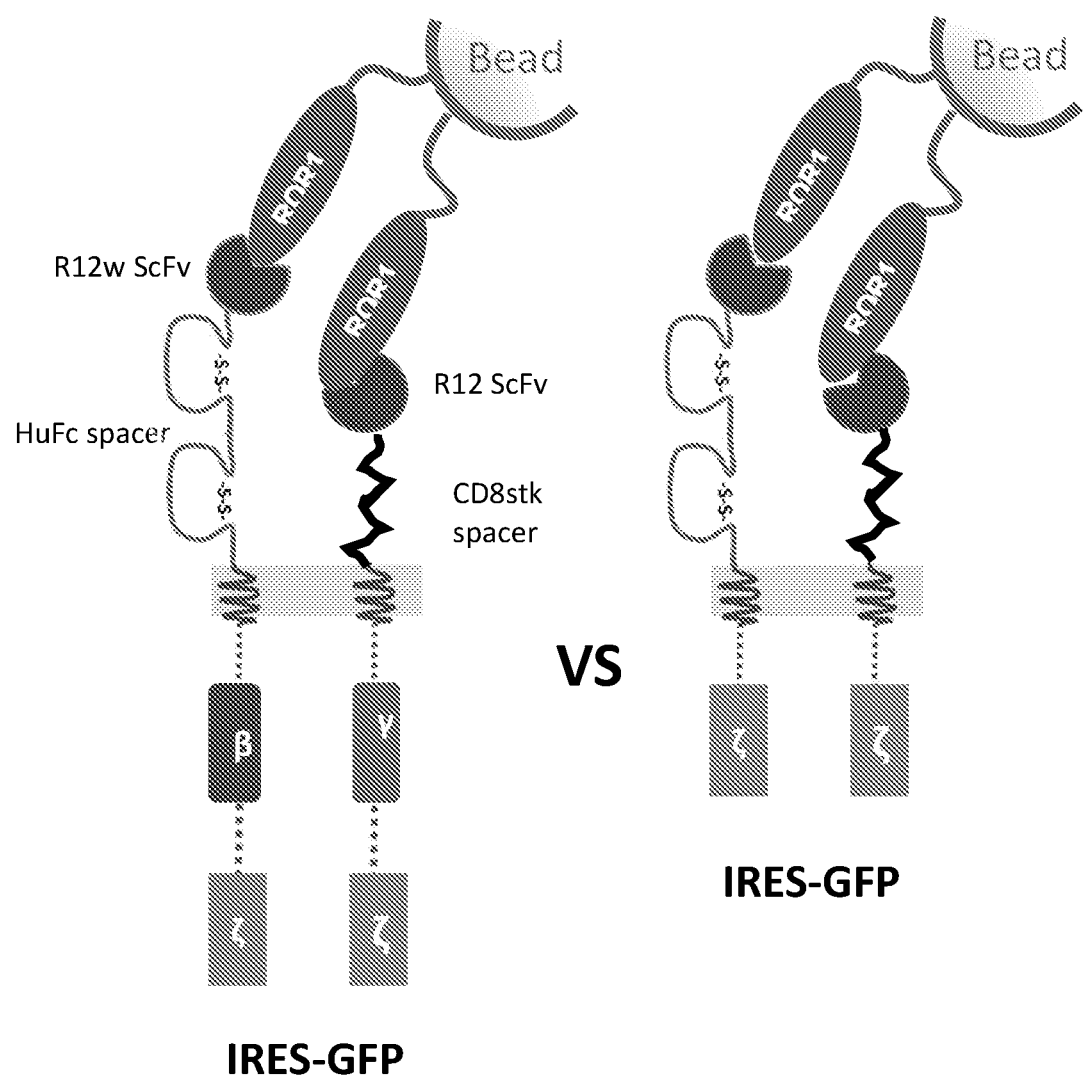

FIG. 12: Schematic diagram illustrating the chimeric receptor systems tested in the proliferation/survival assay described in Example 6. Both chimeric receptors comprises an R12 scFv, so they bind the same epitope on the same antigen: ROR1. The DNA sequence of the first R12 scFv was wobbled to prevent homologous recombination.

Figure 13:
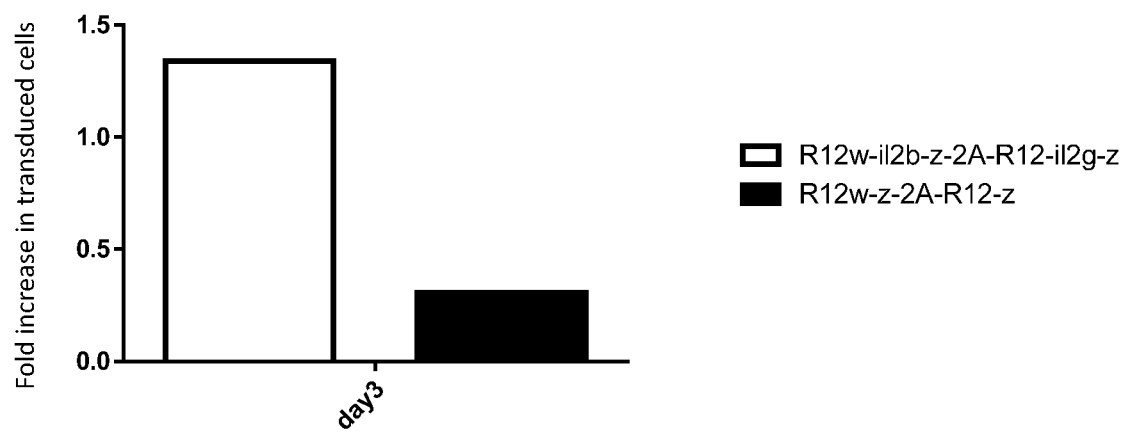

FIG. 13: Graph to show the fold increase of transduced cells when co-cultured with ligand-coated beads. R12w-i12b-z-2A-R12-i12g-z is a construct encoding the 4th generation CAR system illustrated in FIG. 12, which comprises both cytokine receptor endodomains and CD3 zeta endodomains; R12w-z-2A-R12-z is a construct encoding an equivalent chimeric receptor system which lacks the cytokine receptor endodomains.

Figure 14:
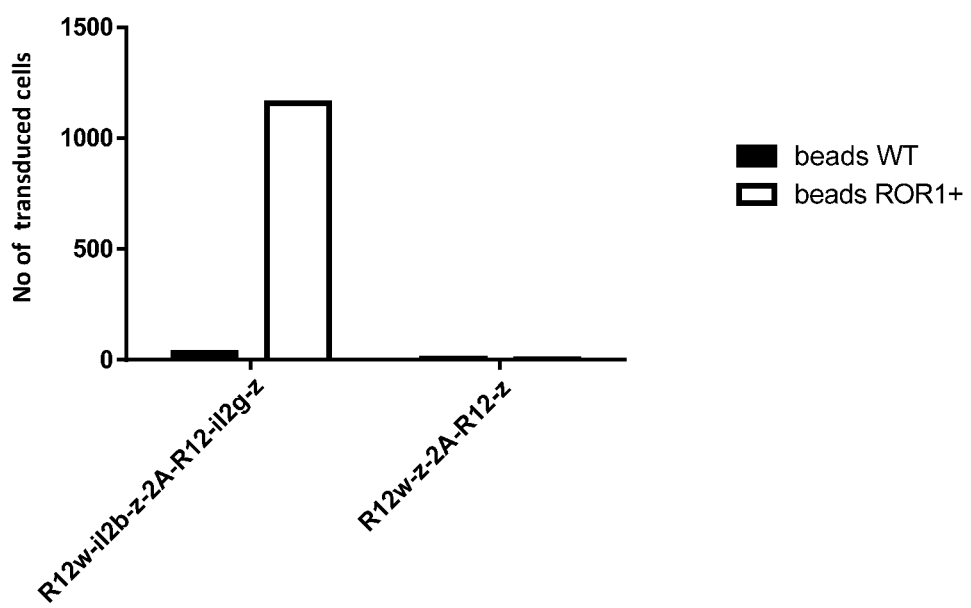

FIG. 14: Graph to show the number of transduced cells after co-culture with ROR1-coated beads after 3 and 6 days.

SUMMARY OF ASPECTS OF THE INVENTION

The present inventors have developed a new type of chimeric receptor (CR) which grafts the binding specificity of, for example, an antibody, on to a combination endodomain which comprises both cytokine receptor endodomain and intracellular T-cell signalling components. Ligation of the receptor provides both cytokine-type and T cell receptor-type activation and proliferation signals to the cell, causing enhanced activation and proliferation, than a conventional CAR.

Enhancement of engraftment, proliferation and survival is particularly useful in the treatment of solid tumours as it enables the CR-expressing cells to engraft and expand in a hostile tumour microenvironment.

Thus in a first aspect, the present invention provides a chimeric receptor comprising:
  a ligand-binding exodomain; and
  an endodomain which comprises:
    (i) a cytokine receptor endodomain; and
    (ii) an intracellular T cell signalling domain.

The ligand-binding exodomain may comprise a heavy chain variable domain ($V_H$) and/or a light chain variable domain ($V_L$).

The cytokine receptor endodomain may comprise or consist of a type I cytokine receptor endodomain α-, β-, or γ-chain. For example, the cytokine receptor endodomain may comprise or consist of:
  (i) IL-2 receptor β-chain endodomain
  (ii) IL-7 receptor α-chain endodomain; or
  (iii) common γ-chain receptor endodomain.

The intracellular T-cell signalling domain may comprise one or more of the following: CD3 zeta endodomain, CD28 endodomain, OX40 endodomain, 4-1BB endodomain, CD2 endodomain, CD27 endodomain, ICOS endodomain, CD40 endodomain.

The arrangement of the intracellular T-cell signalling domain(s) and the cytokine receptor endodomain(s) may be such that when the receptor is expressed at the surface of a cell, the intracellular T-cell signalling domain(s) is/are positioned distal to the membrane and the cytokine receptor endodomain(s) is/are positioned proximal to the membrane on the intracellular cell surface.

In a second aspect the present invention provides a chimeric receptor system.

In a first embodiment of the second aspect of the invention, the chimeric receptor system comprises at least two chimeric receptors according to the first aspect of the invention.

In this first embodiment, the chimeric receptor system comprises a first chimeric receptor which comprises a first cytokine receptor endodomain, and a second chimeric receptor which comprises a second cytokine receptor endodomain. The first cytokine receptor endodomain is complementary to the second cytokine receptor endodomain.

The first chimeric receptor and the second chimeric receptor may bind to different epitopes of the same antigen.

Alternatively, the first chimeric receptor and the second chimeric receptor may bind to the same epitope of the same antigen.

Alternatively, the ligand binding domain of the first chimeric receptor and the ligand binding domain of the second chimeric receptor may have complementary ligand-binding domains, such that together they are capable of ligand binding.

The term "complementary" indicates that the first and second cytokine endodomains associate leading to cell signalling.

The first cytokine receptor endodomain may be or comprise a type 1 cytokine receptor endodomain α- or β-chain, and the second cytokine receptor endodomain may be or comprise a type 1 cytokine receptor endodomain γ-chain, such that when the first chimeric receptor and the second chimeric receptor bind to the antigen, cytokine signalling through the α-/β-chain and γ-chain occurs.

The first chimeric receptor may comprise a CD3 zeta endodomain, and the second chimeric receptor may comprise one or more co-stimulatory domain(s) selected from CD28 endodomain, OX40 endodomain and 4-1BB endodomain.

Alternatively, both the first and second chimeric receptors may comprise an intracellular signalling domain such as the CD3 zeta endodomain.

In a second embodiment of the second aspect of the invention, the chimeric receptor system comprises a chimeric receptor according to the first aspect of the invention and an intracellular fusion protein.

In this second embodiment, the chimeric receptor comprises a first cytokine receptor endodomain, and the intracellular fusion protein comprises a second cytokine receptor endodomain.

The first cytokine receptor endodomain is complementary to the second cytokine receptor endodomain.

The chimeric receptor may comprise a type I cytokine receptor endodomain α- or β-chain, and the intracellular fusion protein may comprise a type I cytokine receptor endodomain γ-chain, or vice versa.

The chimeric receptor may comprise a CD3 zeta endodomain, and the intracellular fusion protein may comprise one or more co-stimulatory domain(s) selected from CD28 endodomain, OX40 endodomain and 4-1BB endodomain, or vice versa.

The chimeric receptor may comprise a CD3 zeta endodomain, and the intracellular fusion protein may lack an intracellular signalling domain.

The intracellular fusion protein may comprise a domain which binds to a phosphorylated CD3 zeta endodomain, such as a ZAP70 SH2 domain. When the chimeric receptor binds the target antigen, this leads to phosphorylation of the CD3 zeta endodomain. The ZAP70 SH2 domain of the intracellular fusion protein binds to the phosphorylated CD3 zeta endodomain, bringing the first and second cytokine receptor endodomains together.

In a third embodiment of the second aspect of the invention, the chimeric receptor system comprises a chimeric receptor according to the first aspect of the invention and a transmembrane protein.

The chimeric receptor comprises a first cytokine receptor endodomain, and the transmembrane protein comprises a second cytokine receptor endodomain. The first cytokine receptor endodomain is complementary to the second cytokine receptor endodomain.

The transmembrane protein may lack a ligand binding exodomain. The transmembrane protein may be tethered to the cell membrane, for example via a transmembrane domain or a myristoylation group.

The chimeric receptor may comprise a type I cytokine receptor endodomain α- or β-chain, and the transmembrane protein may comprise a type I cytokine receptor endodomain γ-chain, or vice versa.

The chimeric receptor may comprise a CD3 zeta endodomain, and the transmembrane protein may comprise one or more co-stimulatory domain(s) selected from CD28 endodomain, OX40 endodomain and 4-1BB endodomain.

The chimeric receptor may comprise a CD3 zeta endodomain, and the transmembrane protein may lack an intracellular signalling domain and/or a costimulatory domain.

The transmembrane protein may comprise a domain which binds to a phosphorylated CD3 zeta endodomain, such as a ZAP70 SH2 domain. When the chimeric receptor binds the target antigen, this leads to phosphorylation of the CD3 zeta endodomain. The ZAP70 SH2 domain of the transmembrane protein binds to the phosphorylated CD3 zeta endodomain, bringing the first and second cytokine receptor endodomains together.

In a third aspect, the present invention provides a cell which comprises a chimeric receptor according to the first aspect of the invention or a chimeric receptor system according to the second aspect of the invention.

In a first embodiment of the third aspect of the invention, the cell comprises a cell receptor system which comprises a first chimeric receptor and a second chimeric receptor.

The cell may comprise a first chimeric receptor and a second chimeric receptor which bind different epitopes on the same antigen.

The cell may alternatively comprise a first chimeric receptor and a second chimeric receptor which bind the same epitope on the same antigen.

The cell may alternatively comprise a first chimeric receptor and a second chimeric receptor which have complementary ligand-binding domains, such that together the ligand-binding domain of the first chimeric receptor and the ligand binding domain of the second chimeric receptor are capable of ligand binding.

The first chimeric receptor may comprise a first cytokine receptor endodomain and the second chimeric receptor may comprise a second cytokine receptor endodomain, and the first and second cytokine receptor endodomains may be capable of associating leading to cell signalling.

For example, the first chimeric receptor may comprise a type I cytokine receptor endodomain α- or β-chain, and the second chimeric receptor may comprise a type I cytokine receptor endodomain γ-chain, such that when the first chimeric receptor and the second chimeric receptor bind the antigen, combined signalling through the α-/β-chain and γ-chain occurs.

The first chimeric receptor may comprise a CD3 zeta endodomain; and the second chimeric receptor may comprise one or more co-stimulatory domain(s) selected from, for example, CD3 zeta endodomain, CD28 endodomain, OX40 endodomain, 4-1BB endodomain, CD2 endodomain, CD27 endodomain, ICOS endodomain and CD40 endodomain.

A cell according to the second aspect of the invention may also comprise a second receptor comprising:
 a ligand-binding exodomain; and
 an endodomain which comprises a cytokine receptor endodomain which is complementary to the cytokine receptor endodomain of the chimeric receptor;
which second receptor lacks an intracellular T cell signalling domain.

In a second embodiment of the third aspect of the invention, the cell comprises a chimeric receptor according to the first aspect of the invention and an intracellular fusion protein as defined above.

The intracellular fusion protein may comprise a ZAP70 SH2 domain.

In a third embodiment of the third aspect of the invention the cell comprises a chimeric receptor according to the first aspect of the invention and a transmembrane protein as defined above.

In a fourth aspect, the present application provides a nucleic acid sequence capable of encoding a chimeric receptor according to the first aspect of the invention.

In a fifth aspect there is provided a nucleic acid construct which encodes a chimeric receptor system according to the second aspect of the invention.

In a first embodiment of the fifth aspect of the invention, the nucleic acid construct comprises a first nucleic acid sequence encoding a first chimeric receptor and a second nucleic acid sequence encoding a second chimeric receptor.

The nucleic acid construct may have the structure:

AgB1-spacer1-TM1-endo1-coexpr-AbB2-spacer2-TM2-endo2 in which

AgB1 is a nucleic acid sequence encoding the antigen-binding domain of the first chimeric receptor;

spacer 1 is a nucleic acid sequence encoding the spacer of the first chimeric receptor;

TM1 is a nucleic acid sequence encoding the transmembrane domain of the first chimeric receptor;

endo 1 is a nucleic acid sequence encoding the endodomain of the first chimeric receptor;

coexpr is a nucleic acid sequence enabling co-expression of both chimeric receptors AgB2 is a nucleic acid sequence encoding the antigen-binding domain of the second chimeric receptor;

spacer 2 is a nucleic acid sequence encoding the spacer of the second chimeric receptor;

TM2 is a nucleic acid sequence encoding the transmembrane domain of the second chimeric receptor;

endo 2 is a nucleic acid sequence encoding the endodomain of the second chimeric receptor.

In the nucleic acid construct of the fifth aspect of the invention, endo 1 may comprise a nucleic acid sequence encoding a first chain of a cytokine receptor endodomain, and a nucleic acid sequence encoding a first intracellular T cell signalling domain; and endo 2 may comprise a nucleic acid sequence encoding a second chain of a cytokine receptor endodomain and a nucleic acid sequence encoding a second intracellular T cell signalling domain.

The coexpr may encode a sequence comprising a self-cleaving peptide.

Alternative codons may be used in regions of sequence encoding the same or similar amino acid sequences, in order to avoid homologous recombination.

In a second embodiment of the fifth aspect of the invention there is provided a nucleic acid construct which comprises a first nucleic acid sequence encoding a chimeric receptor according to the first aspect of the invention and a second nucleic acid sequence encoding an intracellular fusion protein.

The nucleic acid construct may have the structure:

AgB1-spacer1-TM1-endo1-coexpr-domain2-endo2 in which

AgB1 is a nucleic acid sequence encoding the antigen-binding domain of the chimeric receptor;

spacer 1 is a nucleic acid sequence encoding the spacer of the chimeric receptor;

TM1 is a nucleic acid sequence encoding the transmembrane domain of the chimeric receptor;

endo 1 is a nucleic acid sequence encoding the endodomain of the chimeric receptor;

coexpr is a nucleic acid sequence enabling co-expression of both the chimeric receptor and the intracellular fusion protein domain2 is a nucleic acid sequence encoding a second domain of the intracellular fusion protein;

endo 2 is a nucleic acid sequence encoding the cytokine receptor endodomain of the intracellular fusion protein.

The second domain, "domain2", may encode a sequence capable of binding to a phosphorylated CD3 zeta domain. In this respect, "domain2" may be "ZAP70", a nucleic acid sequence encoding a ZAP70 SH2 domain.

In a third embodiment of the fifth aspect of the invention there is provided a nucleic acid construct which comprises a first nucleic acid sequence encoding a chimeric receptor and a second nucleic acid sequence encoding a transmembrane protein.

The nucleic acid construct may have the structure:

AgB1-spacer1-TM1-endo1-coexpr-TM2-endo2 in which

AgB1 is a nucleic acid sequence encoding the antigen-binding domain of the chimeric receptor;

spacer1 is a nucleic acid sequence encoding the spacer of the chimeric receptor;

TM1 is a nucleic acid sequence encoding the transmembrane domain of the chimeric receptor;

endo1 is a nucleic acid sequence encoding the endodomain of the chimeric receptor;

coexpr is a nucleic acid sequence enabling co-expression of both the chimeric receptor and the transmembrane protein, TM2 is a nucleic acid sequence encoding a transmembrane localisation sequence of the transmembrane domain, endo2 is a nucleic acid sequence encoding the cytokine receptor endodomain of the transmembrane protein.

In a sixth aspect, the present invention provides a vector comprising a nucleic acid sequence according to the fourth aspect of the invention or a nucleic acid construct according to the fifth aspect of the invention.

The vector may be, for example, a retroviral vector or a lentiviral vector or a transposon.

In a seventh aspect, there is provided a kit which comprises:
  i) a vector comprising a nucleic acid sequence encoding a first chimeric receptor as defined in the first aspect of the invention; and
  ii) a vector comprising a nucleic acid sequence encoding a second chimeric receptor as defined in the first aspect of the invention.

There is also provided a kit which comprises:
  i) a vector comprising a nucleic acid sequence encoding a chimeric receptor as defined in the first aspect of the invention; and
  ii) a vector comprising a nucleic acid sequence encoding a second receptor or an intracellular fusion protein as defined above.

There is also provided a kit which comprises:
  i) a vector comprising a nucleic acid sequence encoding a chimeric receptor as defined in the first aspect of the invention; and
  ii) a vector comprising a nucleic acid sequence encoding a transmembrane protein as defined above.

In an eighth aspect, there is provided a method for making a cell according to the third aspect of the invention, which comprises the step of introducing: a nucleic acid sequence according to the fourth aspect of the invention; a nucleic acid construct according to the fifth aspect of the invention; a vector according to the sixth aspect of the invention; or a kit of vectors according to the seventh aspect of the invention, into a cell.

The cell may be from a sample isolated from a subject.

In a ninth aspect there is provided a pharmaceutical composition comprising a plurality of cells according to the third aspect of the invention.

In a tenth aspect there is provided a method for treating and/or preventing a disease, which comprises the step of administering a pharmaceutical composition according to the ninth aspect of the invention to a subject.

The method may comprise the following steps:
(i) isolation of a cell-containing sample from a subject;
(ii) transduction or transfection of the cells with: a nucleic acid sequence according to the fourth aspect of the invention; a nucleic acid construct according to the fifth aspect of the invention; a vector according to the sixth aspect of the invention; or a kit of vectors according to the seventh aspect of the invention; and
(iii) administering the cells from (ii) to a the subject.

The sample may be a T-cell containing sample.

The disease may be a cancer.

There is also provided a pharmaceutical composition according to the ninth aspect of the invention for use in treating and/or preventing a disease.

There is also provided the use of a cell according to the third aspect of the invention in the manufacture of a medicament for treating and/or preventing a disease.

DETAILED DESCRIPTION

Chimeric Receptor (CR)

A chimeric receptor (CR) is a molecule which comprises a cytokine receptor endodomain and a heterologous ligand-binding exodomain. The endodomain of the chimeric receptor may also comprise an intracellular T cell signalling domain.

A chimeric receptor may therefore comprise:
(i) a ligand binding exodomain;
(ii) an optional spacer;
(iii) a transmembrane domain;
(iv) a cytokine-receptor endodomain; and
(v) an intracellular T-cell signalling domain.

Cytokine Receptors and Signalling

Many cell functions are regulated by members of the cytokine receptor superfamily. Signalling by these receptors depends upon their association with Janus kinases (JAKs), which couple ligand binding to tyrosine phosphorylation of signalling proteins recruited to the receptor complex. Among these are the signal transducers and activators of transcription (STATs), a family of transcription factors that contribute to the diversity of cytokine responses.

When the chimeric receptor of the invention binds its ligand, one or more of the following intracellular signaling pathways may be initiated:
(i) the JAK-STAT pathway
(ii) the MAP kinase pathway; and
(iii) the Phosphoinositide 3-kinase (PI3K) pathway.

The JAK-STAT system consists of three main components: (1) a receptor (2) Janus kinase (JAK) and (3) Signal Transducer and Activator of Transcription (STAT).

JAKs, which have tyrosine kinase activity, bind to cell surface cytokine receptors. The binding of the ligand to the receptor triggers activation of JAKs. With increased kinase activity, they phosphorylate tyrosine residues on the receptor and create sites for interaction with proteins that contain phosphotyrosine-binding SH2 domains. STATs possessing SH2 domains capable of binding these phosphotyrosine residues are recruited to the receptors, and are themselves tyrosine-phosphorylated by JAKs. These phosphotyrosines then act as binding sites for SH2 domains of other STATs, mediating their dimerization. Different STATs form hetero- or homodimers. Activated STAT dimers accumulate in the cell nucleus and activate transcription of their target genes.

Cytokine Receptor Endodomain

The chimeric receptor of the present invention comprises an endodomain which causes "cytokine-type" cell signalling (either alone or when in the presence of another chimeric receptor) when the exodomain binds its ligand.

The cytokine receptor endodomain may be derived from a type I cytokine receptor. Type I cytokine receptors share a common amino acid motif (WSxWS) in the extracellular portion adjacent to the cell membrane.

The cytokine receptor endodomain may be derived from a type II cytokine receptor. Type II cytokine receptors include those that bind type I and type II interferons, and those that bind members of the interleukin-10 family (interleukin-10, interleukin-20 and interleukin-22).

Type I cytokine receptors include:
(i) Interleukin receptors, such as the receptors for IL-2, IL-3, IL-4, IL-5, IL-6, IL-7, IL-9, IL-11, IL-12, IL13, IL-15, IL-21, IL-23 and IL-27;
(ii) Colony stimulating factor receptors, such as the receptors for erythropoietin, GM-CSF, and G-CSF; and
(iii) Hormone receptor/neuropeptide receptor, such as hormone receptor and prolactin receptor Members of the type I cytokine receptor family comprise different chains, some of which are involved in ligand/cytokine interaction and others that are involved in signal transduction. For example the IL-2 receptor comprises an α-chain, a β-chain and a γ-chain.

The IL-2 receptor common gamma chain (also known as CD132) is shared between the IL-2 receptor, IL-4 receptor, IL-7 receptor, IL-9 receptor, IL-13 receptor and IL-15 receptor.

IL-2

IL-2 binds to the IL-2 receptor, which has three forms, generated by different combinations of three different proteins, often referred to as "chains": α, β and γ; these subunits are also parts of receptors for other cytokines. The β and γ chains of the IL-2R are members of the type I cytokine receptor family.

The three receptor chains are expressed separately and differently on various cell types and can assemble in different combinations and orders to generate low, intermediate, and high affinity IL-2 receptors.

The α chain binds IL-2 with low affinity, the combination of β and γ together form a complex that binds IL-2 with intermediate affinity, primarily on memory T cells and NK cells; and all three receptor chains form a complex that binds IL-2 with high affinity (Kd~10-11 M) on activated T cells and regulatory T cells.

The three IL-2 receptor chains span the cell membrane and extend into the cell, thereby delivering biochemical signals to the cell interior. The alpha chain does not participate in signalling, but the beta chain is complexed with the tyrosine phosphatase JAK1. Similarly the gamma chain complexes with another tyrosine kinase called JAK3. These enzymes are activated by IL-2 binding to the external domains of the IL-2R.

IL-2 signalling promotes the differentiation of T cells into effector T cells and into memory T cells when the initial T cells are also stimulated by an antigen. Through their role in the development of T cell immunologic memory, which depends upon the expansion of the number and function of antigen-selected T cell clones, they also have a key role in long-term cell-mediated immunity.

The chimeric receptor of the present invention may comprise the IL-2 receptor β-chain and/or the IL-2 receptor (i.e. common) γ-chain The amino acid sequences for the endodomains of the IL-2 β-chain and common γ-chain are shown as SEQ ID No. 1 and 2

SEQ ID No. 1: Endodomain derived from human common gamma chain:
ERTMPRIPTLKNLEDLVTEYHGNFSAWSGVSKGLAESLQPDYSERLCLVS

EIPPKGGALGEGPGASPCNQHSPYWAPPCYTLKPET

SEQ ID No. 2: Endodomain derived from human IL-2Rβ:
NCRNTGPWLKKVLKCNTPDPSKFFSQLSSEHGGDVQKWLSSPFPSSSFSP

GGLAPEISPLEVLERDKVTQLLLQQDKVPEPASLSSNHSLTSCFTNQGYF

FFHLPDALEIEACQVYFTYDPYSEEDPDEGVAGAPTGSSPQPLQPLSGED

DAYCTFPSRDDLLLFSPSLLGGPSPPSTAPGGSGAGEERMPPSLQERVPR

DWDPQPLGPPTPGVPDLVDFQPPPELVLREAGEEVPDAGPREGVSFPWSR

PPGQGEFRALNARLPLNTDAYLSLQELQGQDPTHLV

The term "derived from" means that the endodomain of the chimeric receptor of the invention has the same sequence as the wild-type sequence of the endogenous molecule, or a variant thereof which retains the ability to form a complex with JAK-1 or JAK-3 and activate one of the signalling pathways mentioned above.

A "variant" sequence having at least 80, 85, 90, 95, 98 or 99% sequence identity to the wild-type sequence (e.g. SEQ ID Nos. 1 or 2), providing that the variant sequence retains the function of the wild-type sequence i.e. the ability to form a complex with JAK-1 or JAK-3 and activate, for example, the JAK-STAT signalling pathway.

The percentage identity between two polypeptide sequences may be readily determined by programs such as BLAST which is freely available at http [COLON SLASH SLASH] blast.ncbi.nlm.nih.gov.

IL-7

The interleukin-7 receptor is made up of two chains: the interleukin-7 receptor-α chain (CD127) and common-γ chain receptors (CD132). The common-γ chain receptors is shared with various cytokines, including interleukin-2, -4, -9, and -15. Interleukin-7 receptor is expressed on various cell types, including naive and memory T cells.

The interleukin-7 receptor plays a critical role in the development of lymphocytes, especially in V(D)J recombination. IL-7R also controls the accessibility of a region of the genome that contains the T-cell receptor gamma gene, by STAT5 and histone acetylation. Knockout studies in mice suggest that blocking apoptosis is an essential function of this protein during differentiation and activation of T lymphocytes.

The chimeric receptor of the present invention may comprise the IL-7 receptor α-chain and/or the IL-7 receptor (i.e. common) γ-chain, or a variant thereof.

The amino acid sequence for the endodomain of the IL-7 α-chain is shown as SEQ ID No. 3.

Endodomain derived from human IL-7Rα:
SEQ ID No. 3
KKRIKPIVWPSLPDHKKTLEHLCKKPRKNLNVSFNPESFLDCQIHRVDD

IQARDEVEGFLQDTFPQQLEESEKQRLGGDVQSPNCPSEDVVITPESFG

-continued

RDSSLTCLAGNVSACDAPILSSSRSLDCRESGKNGPHVYQDLLLSLGTT

NSTLPPPFSLQSGILTLNPVAQGQPILTSLGSNQEEAYVTMSSFYQNQ

Monomeric Chimeric Receptor Systems

Chimeric antigen receptors are usually homodimers of two identical chains.

The chimeric receptor of the invention can be a homodimer, or a monomer which is brought into association with another chimeric receptor monomer in the presence of ligand.

In particular, the chimeric receptor may be a monomer which comprises:
  (i) an exodomain;
  (ii) a transmembrane domain;
  (iii) a cytokine-receptor endodomain; and
  (v) an intracellular T-cell signalling domain.

The exodomain may comprise a ligand-binding domain such as an scFv. A cell may comprise two monomeric CRs in which the ligand binding domain of the first CR and the ligand-binding domain of the second CR bind to different epitopes on the same ligand.

Alternatively, the exodomain may comprise a domain which, when brought together with the exodomain of another chimeric receptor, produces a functional ligand binding domain. For example, one monomeric chimeric receptor may comprise $V_H$ and the second chimeric receptor comprises $V_L$ of an antibody.

A monomeric cytokine receptor may also comprise one or more intracellular T cell signalling domain(s). For example, the receptor may comprise one or more of the following: CD3 zeta endodomain, CD28 endodomain, OX40 endodomain, 4-1BB endodomain, CD2 endodomain, CD27 endodomain, ICOS endodomain, CD40 endodomain.

Dual Chimeric Receptor Systems

Where a cell comprises two homodimeric or monomeric chimeric receptors, they may have "complementary" cytokine receptor endodomains. Complementary cytokine receptor endodomains are capable of associating with each other to induce cytokine-type signalling.

Examples of complementary cytokine receptor endodomains are given in the table below. In the dual CR system of the invention, one CR may comprise the first cytokine receptor endodomain and the other CR may comprise the second cytokine receptor endodomain

| First cytokine receptor endodomain | Second cytokine receptor endodomain |
|---|---|
| IL2-receptor beta chain | Common gamma chain |
| IL7-receptor alpha chain | Common gamma chain |

The dual chimeric receptor system of the invention comprises one or more intracellular T cell signalling domains. The intracellular T cell signalling domains may be "shared" between the two homodimeric or monomeric chimeric receptors, or one receptor may comprise intracellular T cell signalling domain(s) and the other one not. Some possible combinations are summarised in the following Table:

| Intracellular T cell signalling domains in the first cytokine receptor | Intracellular T cell signalling domains in the second cytokine receptor |
|---|---|
| CD3 zeta | None |
| CD3 zeta and one or more co-stimulatory domains | None |

| Intracellular T cell signalling domains in the first cytokine receptor | Intracellular T cell signalling domains in the second cytokine receptor |
|---|---|
| CD3 zeta | CD3 zeta |
| CD3 zeta and one or more co-stimulatory domains | CD3 zeta and one or more co-stimulatory domains |
| CD3 zeta | CD3 zeta and one or more co-stimulatory domains |
| CD3 zeta | One or more co-stimulatory domains |
| CD3 zeta and one or more co-stimulatory domains | One or more co-stimulatory domains |

For example, one receptor may comprise a CD3 zeta endodomain and the other receptor may comprise one or more co-stimulatory domains, such as CD3 zeta endodomain, CD28 endodomain, OX40 endodomain, 4-1BB endodomain, CD2 endodomain, CD27 endodomain, ICOS endodomain and/or CD40 endodomain.

ZAP70 Chimeric Receptor Systems

In one embodiment of the invention, the chimeric receptor is expressed in the cell along with an intracellular fusion protein. The intracellular fusion protein comprises a cytokine receptor endodomain. The intracellular fusion protein may comprise a domain which binds to a phosphorylated CD3 zeta endodomain, such as a ZAP70 SH2 domain. This embodiment is illustrated schematically in FIG. 4.

ZAP70 is a protein normally expressed near the surface membrane of T cells and natural killer cells. It is part of the T cell receptor (TCR), and plays a critical role in T-cell signalling. Its molecular weight is 70 kDa, and is composed of 2 N-terminal SH2 domains and a C-terminal kinase domain. It is a member of the protein-tyrosine kinase family.

The earliest step in T cell activation is the recognition of a peptide MHC-complex on the target cell by the TCR. This initial event causes the close association of Lck kinase with the cytoplasmic tail of CD3-zeta in the TCR complex. Lck then phosphorylates tyrosine residues in the cytoplasmic tail of CD3-zeta which allows the recruitment of ZAP70. ZAP70 is an SH2 containing kinase that plays a pivotal role in T cell activation following engagement of the TCR. Tandem SH2 domains in ZAP70 bind to the phosphorylated CD3 resulting in ZAP70 being phosphorylated and activated by Lck or by other ZAP70 molecules in trans. Active ZAP70 is then able to phosphorylate downstream membrane proteins, key among them the linker of activated T cells (LAT) protein. LAT is a scaffold protein and its phosphorylation on multiple residues allows it to interact with several other SH2 domain-containing proteins including Grb2, PLC-g and Grap which recognize the phosphorylated peptides in LAT and transmit the T cell activation signal downstream ultimately resulting in a range of T cell responses.

An example ZAP70 protein is the human ZAP70 protein having the UniProtKB accession number P43403. This exemplified sequence is 619 amino acids in length and is shown as SEQ ID NO: 22.

ZAP70 amino acid sequence
(SEQ ID NO: 22)
MPDPAAHLPFFYGSISRAEAEEHLKLAGMADGLFLLRQCLRSLGGYVLS

LVHDVRFHHFPIERQLNGTYAIAGGKAHCGPAELCEFYSRDPDGLPCNL

RKPCNRPSGLEPQPGVFDCLRDAMVRDYVRQTWKLEGEALEQAIISQAP

QVEKLIATTAHERMPVVYHSSLTREEAERKLYSGAQTDGKFLLRPRKEQ

GTYALSLIYGKTVYHYLISQDKAGKYCIPEGTKFDTLWQLVEYLKLKAD

GLIYCLKEACPNSSASNASGAAAPTLPAHPSTLTHPQRRIDTLNSDGYT

PEPARITSPDKPRPMPMDTSVYESPYSDPEELKDKKLFLKRDNLLIADI

ELGCGNFGSVRQGVYRMRKKQIDVAIKVLKQGTEKADTEEMMREAQIMH

QLDNPYIVRLIGVCQAEALMLVMEMAGGGPLHKFLVGKREEIPVSNVAE

LLHQVSMGMKYLEEKNFVHRDLAARNVLLVNRHYAKISDFGLSKALGAD

DSYYTARSAGKWPLKVVYAPECINFRKFSSRSDVWSYGVTMWEALSYGQ

KPYKKMKGPEVMAFIEQGKRMECPPECPPELYALMSDCWIYKWEDRPDF

LTVEQRMRACYYSLASKVEGPPGSTQKAEAACA

The ZAP70 sequence shown as SEQ ID No. 22 comprises tandem SH2 domains. SH2 1 comprises amino acids Nos 10-102 and SH2 2 comprises amino acid Nos 163-254 of this sequence. The ZAP70 SH2 domain may comprise SH2 1, SH2 2 or both SH2 domains.

The fusion protein may comprise tandem ZAP70 SH2 domains. For example, the fusion protein may comprise the sequence shown as SEQ ID NO: 23.

ZAP70 SH2 domain
(SEQ ID NO: 23)
MPDPAAHLPFFYGSISRAEAEEHLKLAGMADGLFLLRQCLRSLGGYVLSL

VHDVRFHHFPIERQLNGTYAIAGGKAHCGPAELCEFYSRDPDGLPCNLRK

PCNRPSGLEPQPGVFDCLRDAMVRDYVRQTWKLEGEALEQAIISQAPQVE

KLIATTAHERMPVVYHSSLTREEAERKLYSGAQTDGKFLLRPRKEQGTYA

LSLIYGKTVYHYLISQDKAGKYCIPEGTKFDTLWQLVEYLKLKADGLIYC

LKEACPNSSASNASGAAAPTLPAHPSTLTHP

The fusion protein may comprise a variant of SEQ ID NO: 23 having at least 80, 85, 90, 95, 98 or 99% sequence identity, provided that the variant sequence is a SH2 domain sequence having the required properties. In other words, the variant sequence must be capable of binding to the phosphorylated tyrosine residues in the cytoplasmic tail of CD3-zeta which allow the recruitment of ZAP70.

In certain embodiments, the fusion protein may comprise the ZAP70 SH2 domain and the ZAP70 kinase domain. For example, the fusion protein may comprise the sequence shown as SEQ ID NO: 22 or a variant thereof having at least 80, 85, 90, 95, 98 or 99% sequence identity.

The fusion protein also comprises a cytokine receptor endodomain. The cytokine receptor endodomain of the fusion protein may be "complementary" to the cytokine receptor endodomain of the chimeric receptor, as defined above. Complementary cytokine receptor endodomains are capable of associating with each other to induce cytokine-type signalling.

Transmembrane Protein

In another embodiment of the invention, the chimeric receptor is expressed in the cell along with a transmembrane protein. The chimeric receptor and the transmembrane protein comprise complementary cytokine receptor endodomains.

The transmembrane protein may be tethered to or associated with the cell membrane. For example, the transmembrane protein may comprise a transmembrane domain, which anchors the protein to the membrane of a cell. Alternatively the transmembrane protein may comprise a myristoyl group.

Myristoylation is a lipidation modification where a myristoyl group, derived from myristic acid, is covalently attached by an amide bond to the alpha-amino group of an N-terminal glycine residue.

The transmembrane protein may also comprise one or more co-stimulatory domains.

The transmembrane protein may lack a ligand-binding exodomain.

Spacer

The chimeric receptor of the present invention may comprise a spacer to connect the antigen-binding domain with the transmembrane domain and spatially separate the antigen-binding domain from the endodomain. A flexible spacer allows to the antigen-binding domain to orient in different directions to enable antigen binding.

Where the cell of the present invention comprises two or more chimeric receptors, the spacers may be the same or different.

The spacer sequence may, for example, comprise an IgG1 Fc region, an IgG1 hinge or a CD8 stalk. The linker may alternatively comprise an alternative linker sequence which has similar length and/or domain spacing properties as an IgG1 Fc region, an IgG1 hinge or a CD8 stalk.

A human IgG1 spacer may be altered to remove Fc binding motifs.

Examples of amino acid sequences for these spacers are given below:

```
(hinge-CH2CH3 of human IgG1)
                                        SEQ ID No. 4
AEPKSPDKTHTCPPCPAPPVAGPSVFLFPPKPKDTLMIARTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGKKD (human CD8 stalk):
                                        SEQ ID No. 5
TTTPAPRPPTPAPTIASQPLSLRPEACRPAAGGAVHTRGLDFACDI (human IgG1 hinge):
                                        SEQ ID No. 6
AEPKSPDKTHTCPPCPKDPK
```

The spacer may be monomeric. Monomeric spacers may be generated by mutation of the cysteine residue(s) responsible for disulphide bond formation (Bridgeman et al (2010) J. Immunol. 184:6938-6949).

Transmembrane Domain

The transmembrane domain is the sequence of a CR that spans the membrane. It may comprise a hydrophobic alpha helix. The transmembrane domain may be derived from CD28, which gives good receptor stability.

Alternatively the transmembrane domain may be derived from a cytokine receptor, for example the same cytokine from which the endodomain is derived.

The transmembrane domain may, for example be derived from IL-2R, IL-7R or IL-15R.

```
Transmembrane derived from human common gamma
chain:
                                        SEQ ID No. 7
VVISVGSMGLIISLLCVYFWL Transmembrane derived from human IL-2Rβ:
                                        SEQ ID No. 8
IPWLGHLLVGLSGAFGFIILVYLLI Transmembrane derived from human IL-7Rα:
                                        SEQ ID No. 9
PILLTISILSFFSVALLVILACVLW Transmembrane derived from human IL-15Rα:
                                        SEQ ID No. 10
AISTSTVLLCGLSAVSLLACYL
```

The term "ligand binding domain" refers to the extracellular portion of the CR which is involved in ligand binding. The ligand-binding domain of a single chimeric receptor may be itself capable of binding the ligand (for example, if it is based on an scFv). Alternatively the ligand-binding domain may be capable of ligand binding when in association with another chimeric receptor (for example, where one CR comprises $V_H$ and one CR comprises $V_L$ of an antibody).

The term "ligand" is used synonymously with "antigen" to mean an entity which is specifically recognised and bound by the antigen-binding domain of the CR or a combination of complementary CR ligand-binding domains.

Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; the binding domain from a natural receptor for the target antigen; a peptide with sufficient affinity for the target ligand; a single domain binder such as a camelid; an artificial binder single as a Darpin; or a single-chain derived from a T-cell receptor.

The amino acid sequence shown in FIG. 5 comprises two CARs, each having a CD22-binding ligand binding domain. One is based on the scFv LT22 and one is based on the scFv RFB4.

Ligand

The CR or CR system of the present invention binds to a ligand.

The ligand may be a soluble ligand such as a tumour secreted factor or a chemokine.

Alternatively, the ligand may be a membrane bound ligand, such as a cell surface antigen.

The term "soluble ligand" is used to indicate a ligand or antigen which is not part of or attached to a cell but which moves freely in the extracellular space, for example in a bodily fluid of the tissue of interest. The soluble ligand may exist in a cell-free state in the serum, plasma or other bodily fluid of an individual.

The soluble ligand may be associated with the presence or pathology of a particular disease, such as cancer.

The soluble ligand may be part of the cancer secretome, i.e. the collection of factors secreted by a tumour, be it from cancer stem cells, non-stem cells or the surrounding stroma. The soluble ligand may be secreted or shed by tumour cells (see next section).

The soluble ligand may be characteristic of a disease or of diseased tissue. It may be found exclusively, or at a higher level in a subject having the disease vs a healthy subject; or in diseased tissue vs healthy tissue. The soluble ligand may be expressed at at least a 2-fold, 5-fold, 10-fold, 100-fold, 1000-fold, 10,000-fold or 100,000 fold higher level a subject having the disease vs a healthy subject; or in diseased tissue vs healthy tissue.

The terms "cell-surface antigen" and "cell-surface ligand" is used synonymously with "membrane-bound antigen" and "membrane-bound ligand" to mean a ligand which is attached to or expressed on the surface of the cell. The cell-surface ligand may, for example, be a transmembrane protein.

The cell on which the cell-surface ligand is found may be a target cell, such as a cancer cell.

The cell-surface ligand may be associated with the presence or pathology of a particular disease, such as cancer. Alternatively the cell-surface ligand may be characteristic of the cell type of the target cell (e.g. B-cell) without being necessarily associated with the diseased state.

Where the cell-surface ligand is characteristic of a disease or of diseased tissue it may be found exclusively, or at a higher level on the relevant cells a subject having the disease vs a healthy subject; or in diseased tissue vs healthy tissue. The cell-surface ligand may be expressed at least a 2-fold, 5-fold, 10-fold, 100-fold, 1000-fold, 10,000-fold or 100,000 fold higher level on a cell of a subject having the disease vs a healthy subject; or in diseased tissue vs healthy tissue.

Tumour Secreted Factor

The ligand recognised by the CR may be a soluble ligand secreted by or shed from a tumour.

This "tumour secreted factor" may, for example, be prostate-specific antigen (PSA), carcinoembryonic antigen (CEA), vascular endothelial growth factor (VEGF) or Cancer Antigen-125 (CA-125).

Cell Surface Antigen

The CR or CR system may recognise a cell-surface antigen, i.e. an entity, such as a transmembrane protein which is expressed on the surface of a target cell, such as a tumour cell.

The CR or CR system may specifically bind a tumour-associated cell-surface antigen.

Various tumour associated antigens (TAA) are known, some of which are shown in Table 1. The antigen-binding domain used in the present invention may be a domain which is capable of binding a TAA as indicated therein.

TABLE 1

| Cancer type | TAA |
| --- | --- |
| Diffuse Large B-cell Lymphoma | CD19, CD20, CD22 |
| Breast cancer | ErbB2, MUC1 |
| AML | CD13, CD33 |
| Neuroblastoma | GD2, NCAM, ALK, GD2 |
| B-CLL | CD19, CD52, CD160 |
| Colorectal cancer | Folate binding protein, CA-125 |
| Chronic Lymphocytic Leukaemia | CD5, CD19 |
| Glioma | EGFR, Vimentin |
| Multiple myeloma | BCMA, CD138 |
| Renal Cell Carcinoma | Carbonic anhydrase IX, G250 |
| Prostate cancer | PSCA, PSMA |
| Bowel cancer | A33 |

Prostate-Cancer Associated Antigens

The CR may specifically bind a cell-surface antigen associated with prostate cancer, such as prostate stem cell antigen (PSCA) or prostate-specific membrane antigen (PSMA).

PSCA is a glycosylphosphatidylinositol-anchored cell membrane glycoprotein. It is is up-regulated in a large proportion of prostate cancers and is also detected in cancers of the bladder and pancreas.

Various anti-PSCA antibodies are known, such as 7F5 (Morgenroth et al (Prostate (2007) 67:1121-1131); 1G8 (Hillerdal et al (2014) BMC Cancer 14:30); and Ha1-4.117 (Abate-Daga et al (2014) 25:1003-1012).

The CR-expressing cell of the invention may comprise an antigen binding domain based on one of these antibodies.

PSMA is is a zinc metalloenzyme that resides in membranes. PSMA is strongly expressed in the human prostate, being a hundredfold greater than the expression in most other tissues. In cancer, it is upregulated in expression and has been called the second-most-upregulated gene in prostate cancer, with increase of 8- to 12-fold over the noncancerous prostate. In addition to the expression in the human prostate and prostate cancer, PSMA is also found to be highly expressed in tumor neovasculature but not normal vasculature of all types of solid tumors, such as kidney, breast, colon, etc.

Various anti-PSMA antibodies are known, such as 7E11, J591, J415, and Hybritech PEQ226.5 and PM2J004.5 each of which binds a distinct epitope of PSMA (Chang et al (1999) Cancer Res 15:3192-8).

The CR of the invention may comprise an antigen binding domain based on one of these antibodies.

For example, the CR may comprise an scFv based on J591, having the sequence shown as SEQ ID No. 11.

(J591 scFv)
SEQ ID No. 11
EVQLQQSGPELKKPGTSVRISCKTSGYTFTEYTIHWVKQSHGKSLEWIG

NINPNNGGTTYNQKFEDKATLTVDKSSSTAYMELRSLTSEDSAVYYCAA

GWNFDYWGQGTTLTVSSGGGGSGGGGSGGGGSDIVMTQSHKFMSTSVGD

RVSIICKASQDVGTAVDWYQQKPGQSPKWYWASTRHTGVPDRFTGSGSG

TDFTLTITNVQSEDLADYFCQQYNSYPLTFGAGTMLDLKR

Signal Peptide

The CR or transmembrane protein described herein may comprise a signal peptide so that when it/they is/are expressed in a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule. Numerous signal peptides are known in the art which are suitable for use with the CR on the invention.

CR Endodomain

The endodomain is the portion of a chimeric receptor or transmembrane protein which is located on the intracellular side of the membrane.

The endodomain is the signal-transmission portion of a classical CAR. After antigen recognition by the antigen binding domain, individual CAR molecules cluster, native CD45 and CD148 are excluded from the synapse and a signal is transmitted to the cell. The same principle holds true for the chimeric receptor of the present invention.

Clustering of the chimeric receptors by kinetic segregation allows the cell signalling to occur via the intracellular T-cell signalling domains The most commonly used signalling domain component is that of CD3-zeta endodomain, which contains 3 ITAMs. This transmits an activation signal to the T cell after antigen is bound. CD3-zeta may not provide a fully competent activation signal and additional co-stimulatory signalling may be needed. For example, chimeric CD28 and OX40 can be used with CD3-Zeta to transmit a proliferative/survival signal, or all three can be used together.

The CR may comprise the CD3-Zeta endodomain alone, the CD3-Zeta endodomain with that of either CD28 or OX40 or the CD28 endodomain and OX40 and CD3-Zeta endodomain.

Where the cell comprises two or more chimeric receptors the intracellular signalling domains may be "shared" between the CR molecules. For example, one CR may comprise a CD3 zeta endodomain and another CR may comprise one or more co-stimulatory domains, such as from CD28, OX40 or 4-1BB.

Where the cell comprises a chimeric receptor and a transmembrane protein, the intracellular signalling domains may be "shared" between the CR and the transmembrane protein. For example, the CR may comprise a CD3 zeta endodomain and the transmembrane protein may comprise one or more co-stimulatory domains, such as from CD28, OX40 or 4-1BB.

The CR or transmembrane protein endodomain may comprise one or more of the following: an ICOS endodomain, a CD27 endodomain, a BTLA endodomain, a CD30 endodomain, a GITR endodomain and an HVEM endodomain.

The endodomain may comprise one or more of the sequences shown as SEQ ID No. 12 to 20 or a variant thereof having at least 80% sequence identity.

```
CD3 Z endodomain
                                     SEQ ID No. 12
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

CD28 and CD3 Zeta endodomains
                                     SEQ ID No. 13
SKRSRLLHSDYMNMTPRRPGPTRKHYQPYAPPRDFAAYRSRVKFSRSADA

PAYQQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALP

PR

CD28, OX40 and CD3 Zeta endodomains
                                     SEQ ID No. 14
SKRSRLLHSDYMNMTPRRPGPTRKHYQPYAPPRDFAAYRSRDQRLPPDAH

KPPGGGSFRTPIQEEQADAHSTLAKIRVKFSRSADAPAYQQGQNQLYNEL

NLGRREEYDVLDKRRGRDPEMGGKPRRKNPQEGLYNELQKDKMAEAYSEI

GMKGERRRGKGHDGLYQGLSTATKDTYDALHMQALPPR

ICOS endodomain
                                     SEQ ID No. 15
CWLTKKKYSSSVHDPNGEYMFMRAVNTAKKSRLTDVTL CD27 endodomain
                                     SEQ ID No. 16
QRRKYRSNKGESPVEPAEPCHYSCPREEEGSTIPIQEDYRKPEPACSP BTLA endodomain
                                     SEQ ID No. 17
RRHQGKQNELSDTAGREINLVDAHLKSEQTEASTRQNSQVLLSETGIYDN

DPDLCFRMQEGSEVYSNPCLEENKPGIVYASLNHSVIGPNSRLARNVKEA

PTEYASICVRS
```

```
CD30 endodomain
                                     SEQ ID No. 18
HRRACRKRIRQKLHLCYPVQTSQPKLELVDSRPRRSSTQLRSGASVTEPV

AEERGLMSQPLMETCHSVGAAYLESLPLQDASPAGGPSSPRDLPEPRVST

EHTNNKIEKIYIMKADTVIVGTVKAELPEGRGLAGPAEPELEEELEADHT

PHYPEQETEPPLGSCSDVMLSVEEEGKEDPLPTAASGK

GITR endodomain
                                     SEQ ID No. 19
QLGLHIWQLRSQCMWPRETQLLLEVPPSTEDARSCQFPEEERGERSAEEK

GRLGDLWV

HVEM endodomain
                                     SEQ ID No. 20
CVKRRKPRGDVVKVIVSVQRKRQEAEGEATVIEALQAPPDVTTVAVEETI

PSFTGRSPNH
```

A variant sequence may have at least 80%, 85%, 90%, 95%, 98% or 99% sequence identity to SEQ ID No. 12 to 20, provided that the sequence provides an effective intracellular signalling domain.

Nucleic Acid

The present invention also provides a nucleic acid encoding a CR of the invention. The nucleic acid may have the structure:

AgB-spacer-TM-endo in which

AgB1 is a nucleic acid sequence encoding the antigen-binding domain of the CR;

spacer 1 is a nucleic acid sequence encoding the spacer of the CR;

TM1 is a nucleic acid sequence encoding the transmembrane domain of the CR;

endo 1 is a nucleic acid sequence encoding the endodomain of the CR.

Nucleic Acid Construct

The present invention further provides a nucleic acid construct which encodes a chimeric receptor system of the invention.

The nucleic acid construct may comprise a first nucleic acid sequence encoding a first CR as defined in connection with the first aspect of the invention; and a second nucleic acid sequence encoding a second CR as defined in connection with the first aspect of the invention.

The nucleic acid construct may have the structure:

AgB1-spacer1-TM1-endo1-coexpr-AbB2-spacer2-TM2-endo2 in which

AgB1 is a nucleic acid sequence encoding the antigen-binding domain of the first chimeric receptor;

spacer 1 is a nucleic acid sequence encoding the spacer of the first chimeric receptor;

TM1 is a nucleic acid sequence encoding the transmembrane domain of the first chimeric receptor;

endo 1 is a nucleic acid sequence encoding the endodomain of the first chimeric receptor;

coexpr is a nucleic acid sequence enabling co-expression of both chimeric receptors AgB2 is a nucleic acid sequence encoding the antigen-binding domain of the second chimeric receptor;

spacer 2 is a nucleic acid sequence encoding the spacer of the second chimeric receptor;

TM2 is a nucleic acid sequence encoding the transmembrane domain of the second chimeric receptor;

endo 2 is a nucleic acid sequence encoding the endodomain of the second chimeric receptor.

When the nucleic acid construct is expressed in a cell, such as a T-cell, it encodes a polypeptide which is cleaved at the cleavage site such that the first and second CRs are co-expressed at the cell surface.

The first and second CRs may bind distinct epitopes on the same antigen. Alternatively the first and second CRs may comprise complementary ligand-binding domains which, together, are capable of antigen binding.

The first and second CRs may have complementary cytokine receptor endodomains e.g. one derived from the α or β chain of a cytokine receptor and one derived from the γ chain of the same cytokine receptor.

Alternatively the nucleic acid construct may comprise a first nucleic acid sequence encoding a chimeric receptor according to the first aspect of the invention and a second nucleic acid sequence encoding an intracellular fusion protein.

The nucleic acid construct may have the structure:

AgB1-spacer1-TM1-endo1-coexpr-domain2-endo2 in which

AgB1 is a nucleic acid sequence encoding the antigen-binding domain of the chimeric receptor;

spacer 1 is a nucleic acid sequence encoding the spacer of the chimeric receptor;

TM1 is a nucleic acid sequence encoding the transmembrane domain of the chimeric receptor;

endo 1 is a nucleic acid sequence encoding the endodomain of the chimeric receptor;

coexpr is a nucleic acid sequence enabling co-expression of both the chimeric receptor and the intracellular fusion protein domain2 is a nucleic acid sequence encoding a second domain of the intracellular fusion protein;

endo 2 is a nucleic acid sequence encoding the cytokine receptor endodomain of the intracellular fusion protein.

The second domain, "domain2", may be "ZAP70", a nucleic acid sequence encoding a ZAP70 SH2 domain.

Alternatively the nucleic acid construct may comprise a first nucleic acid sequence encoding a chimeric receptor and a second nucleic acid sequence encoding a transmembrane protein.

The nucleic acid construct may have the structure:

AgB1-spacer1-TM1-endo1-coexpr-TM2-endo2 in which

AgB1 is a nucleic acid sequence encoding the antigen-binding domain of the chimeric receptor;

spacer1 is a nucleic acid sequence encoding the spacer of the chimeric receptor;

TM1 is a nucleic acid sequence encoding the transmembrane domain of the chimeric receptor;

endo1 is a nucleic acid sequence encoding the endodomain of the chimeric receptor;

coexpr is a nucleic acid sequence enabling co-expression of both the chimeric receptor and the transmembrane protein, TM2 is a nucleic acid sequence encoding a membrane localisation domain of the transmembrane domain, endo2 is a nucleic acid sequence encoding the cytokine receptor endodomain of the transmembrane protein.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

In the structure above, "coexpr" is a nucleic acid sequence enabling co-expression of both first and second CRs. It may be a sequence encoding a cleavage site, such that the nucleic acid construct produces comprises two or more CRs, joined by a cleavage site(s). The cleavage site may be self-cleaving, such that when the polypeptide is produced, it is immediately cleaved into individual peptides without the need for any external cleavage activity.

The cleavage site may be any sequence which enables the first and second CRs, to become separated.

The term "cleavage" is used herein for convenience, but the cleavage site may cause the peptides to separate into individual entities by a mechanism other than classical cleavage. For example, for the Foot-and-Mouth disease virus (FMDV) 2A self-cleaving peptide (see below), various models have been proposed for to account for the "cleavage" activity: proteolysis by a host-cell proteinase, autoproteolysis or a translational effect (Donnelly et al (2001) J. Gen. Virol. 82:1027-1041). The exact mechanism of such "cleavage" is not important for the purposes of the present invention, as long as the cleavage site, when positioned between nucleic acid sequences which encode proteins, causes the proteins to be expressed as separate entities.

The cleavage site may be a furin cleavage site.

Furin is an enzyme which belongs to the subtilisin-like proprotein convertase family. The members of this family are proprotein convertases that process latent precursor proteins into their biologically active products. Furin is a calcium-dependent serine endoprotease that can efficiently cleave precursor proteins at their paired basic amino acid processing sites. Examples of furin substrates include proparathyroid hormone, transforming growth factor beta 1 precursor, proalbumin, pro-beta-secretase, membrane type-1 matrix metalloproteinase, beta subunit of pro-nerve growth factor and von Willebrand factor. Furin cleaves proteins just downstream of a basic amino acid target sequence (canonically, Arg-X-(Arg/Lys)-Arg') and is enriched in the Golgi apparatus.

The cleavage site may be a Tobacco Etch Virus (TEV) cleavage site.

TEV protease is a highly sequence-specific cysteine protease which is chymotrypsin-like proteases. It is very specific for its target cleavage site and is therefore frequently used for the controlled cleavage of fusion proteins both in vitro and in vivo. The consensus TEV cleavage site is ENLYFQ\S (where '\' denotes the cleaved peptide bond). Mammalian cells, such as human cells, do not express TEV protease. Thus in embodiments in which the present nucleic acid construct comprises a TEV cleavage site and is expressed in a mammalian cell—exogenous TEV protease must also expressed in the mammalian cell.

The cleavage site may encode a self-cleaving peptide.

A 'self-cleaving peptide' refers to a peptide which functions such that when the polypeptide comprising the proteins and the self-cleaving peptide is produced, it is immediately "cleaved" or separated into distinct and discrete first and second polypeptides without the need for any external cleavage activity.

The self-cleaving peptide may be a 2A self-cleaving peptide from an aphtho- or a cardiovirus. The primary 2A/2B cleavage of the aptho- and cardioviruses is mediated by 2A "cleaving" at its own C-terminus. In apthoviruses, such as foot-and-mouth disease viruses (FMDV) and equine rhinitis A virus, the 2A region is a short section of about 18 amino acids, which, together with the N-terminal residue of protein 2B (a conserved proline residue) represents an autonomous element capable of mediating "cleavage" at its own C-terminus (Donelly et al (2001) as above).

"2A-like" sequences have been found in picornaviruses other than aptho- or cardioviruses, 'picornavirus-like' insect viruses, type C rotaviruses and repeated sequences within *Trypanosoma* spp and a bacterial sequence (Donnelly et al (2001) as above). The cleavage site may comprise one of these 2A-like sequences, such as:

SEQ ID No. 21: RAEGRGSLLTCGDVEENPGP.

The present invention also provides a kit comprising one or more nucleic acid sequence(s) encoding first and second CRs according to the first aspect of the present invention.

Vector

The present invention also provides a vector, or kit of vectors, which comprises one or more nucleic acid sequence(s) encoding a one or more CR(s) according to the first aspect of the invention. Such a vector may be used to introduce the nucleic acid sequence(s) into a host cell so that it expresses a CR according to the first aspect of the invention.

The vector may, for example, be a plasmid or a viral vector, such as a retroviral vector or a lentiviral vector, or a transposon based vector or synthetic mRNA.

The vector may be capable of transfecting or transducing a T cell or a NK cell.

Cell

The present invention provides a cell which comprises one or more CR(s) of the invention. The cell may comprise a CR system as defined above.

The cell may comprise one or more nucleic acid(s) or vector(s) of the present invention.

The cell may be a cytolytic immune cell such as a T cell or an NK cell.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

The cell may be a Natural Killer cell (or NK cell). NK cells form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The CR-expressing cells of the invention may be any of the cell types mentioned above.

T or NK cells according to the first aspect of the invention may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, T or NK cells according to the first aspect of the invention may be derived from ex vivo differentiation of inducible progenitor cells or embryonic progenitor cells to T or NK cells. Alternatively, an immortalized T-cell line which retains its lytic function and could act as a therapeutic may be used.

In all these embodiments, CR-expressing cells are generated by introducing DNA or RNA coding for the or each CR(s) by one of many means including transduction with a viral vector, transfection with DNA or RNA.

The cell of the invention may be an ex vivo T or NK cell from a subject. The T or NK cell may be from a peripheral blood mononuclear cell (PBMC) sample. T or NK cells may be activated and/or expanded prior to being transduced with nucleic acid encoding the molecules providing the CR according to the first aspect of the invention, for example by treatment with an anti-CD3 monoclonal antibody.

The T or NK cell of the invention may be made by:
(i) isolation of a T or NK cell-containing sample from a subject or other sources listed above; and
(ii) transduction or transfection of the T or NK cells with one or more a nucleic acid sequence(s) encoding a CR.

The T or NK cells may then by purified, for example, selected on the basis of expression of the antigen-binding domain of the antigen-binding polypeptide.

Pharmaceutical Composition

The present invention also relates to a pharmaceutical composition containing a plurality of cells according to the invention.

The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The present invention provides a method for treating and/or preventing a disease which comprises the step of administering the cells of the present invention (for example in a pharmaceutical composition as described above) to a subject.

A method for treating a disease relates to the therapeutic use of the cells of the present invention. Herein the cells may be administered to a subject having an existing disease or condition in order to lessen, reduce or improve at least one symptom associated with the disease and/or to slow down, reduce or block the progression of the disease.

The method for preventing a disease relates to the prophylactic use of the cells of the present invention. Herein such cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:
(i) isolating a T or NK cell-containing sample;
(ii) transducing or transfecting such cells with a nucleic acid sequence or vector provided by the present invention;
(iii) administering the cells from (ii) to a subject.

The T or NK cell-containing sample may be isolated from a subject or from other sources, for example as described above. The T or NK cells may be isolated from a subject's own peripheral blood (1st party), or in the setting of a haematopoietic stem cell transplant from donor peripheral blood (2nd party), or peripheral blood from an unconnected donor (3rd party).

The present invention provides a CR- or CR system-expressing cell of the present invention for use in treating and/or preventing a disease.

The invention also relates to the use of a CR-expressing or CR system-expressing cell of the present invention in the manufacture of a medicament for the treatment and/or prevention of a disease.

The disease to be treated and/or prevented by the methods of the present invention may be a cancerous disease, such as bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

Where the ligand recognised by the CR is PSA, PSMA or PSCA, the cancer may be prostate cancer.

The cells of the present invention may be capable of killing target cells, such as cancer cells. The target cell may be characterised by the presence of a tumour secreted ligand or chemokine ligand in the vicinity of the target cell. The target cell may be characterised by the presence of a soluble ligand together with the expression of a tumour-associated antigen (TAA) at the target cell surface.

The cells and pharmaceutical compositions of present invention may be for use in the treatment and/or prevention of the diseases described above.

The cells and pharmaceutical compositions of present invention may be for use in any of the methods described above.

The invention will now be further described by way of Examples, which are meant to serve to assist one of ordinary skill in the art in carrying out the invention and are not intended in any way to limit the scope of the invention.

EXAMPLES

Example 1—In Vitro Testing

T-cells are transduced with retroviral vector coding for standard CARs or CARs which transmit cytokine signals. Non-transduced and transduced T-cells are challenged with target cells expressing the CR cognate target. Activation of the cytokine pathway in response to target antigen can be directly detected by utilizing intracellular antibody staining and flow cytometry to measure the level of phosphorylation of known mediators in the PI3 kinase, MAP Kinase and JAK-STAT pathways. Cytokine signalling can be indirectly determined by measuring T-cell proliferation, apoptosis and phenotype by flow-cytometry.

Example 2—Generation of a "4th Generation" CAR System with Antigen Binding Domains Against Distinct Epitopes of a Target Antigen A 4th generation CAR system was designed having scFvs which bind to different epitopes of the antigen ROR1 (FIG. 6). The first chimeric receptor had an antigen binding domain comprising an R11 scFv, a human Fc spacer, an IL2 receptor β endodomain and a CD3 zeta endodomain; the second chimeric receptor had an antigen binding domain comprising an R12 scFv, a CD8 stalk spacer, an IL2 receptor γ endodomain and a CD3 zeta endodomain. Two control receptor systems were also designed: one which lacked the cytokine receptor endodomains (FIG. 6); and one which lacked the CD3 zeta domains (FIG. 9), but which were otherwise identical to the system described above.

Example 3—a 4th Generation CAR System Shows Increased Proliferation/Survival than an Equivalent CAR System Lacking Cytokine Receptor Endodomains In order to investigate whether the presence of a chimeric receptor system comprising cytokine endodomains provides a proliferation/survival signal, the CTLL2 murine cytotoxic T cell line (ATCC® TIB-214™) was used which requires IL2 for growth. CTLL cells were transduced with a vector expressing one or other of the two chimeric receptor systems shown in FIG. 6. Cell proliferation was assessed after 3 and 6 days of culture either with ROR1-coated beads or uncoated beads.

The results are shown in FIGS. 7 and 8. As shown in FIG. 7, the 4th generation CAR which included cytokine receptor and CD3 zeta endodomains showed a greater fold-enrichment in transduced cells when co-cultured with ligand at both day 3 and day 6, than an equivalent chimeric receptor system which lacked cytokine receptor endodomains. As shown in FIG. 8, the presence of ligand greatly increased cell survival/proliferation at both day 3 and day 6 for cells expressing the 4th generation CAR, whereas the presence of ligand had little effect on the proliferation/survival of cells expressing an equivalent chimeric receptor system lacking cytokine receptor endodomains.

Example 4—A 4th Generation CAR System Shows Increased Target Cell Killing and IFNg Release than an Equivalent CAR System Lacking CD3 Zeta Endodomains Next it was investigated whether a 4th generation CAR which included cytokine receptor and CD3 zeta endodomains is capable of killing target cells. Healthy donor PBMCs were transduced with a vector expressing one or other of the two chimeric receptor systems shown in FIG. 9. The transduced cells were co-cultured with either SupT1 cells or SupT1 target cells expressing ROR1 at a 10:1 E:T ratio for 48 hours. Killing of target cells was then analysed by FACS and an ELISA was used to assay IFNγ secretion.

As shown in FIG. 10, the 4th generation CAR which included cytokine receptor and CD3 zeta endodomains was capable of killing ROR1-expressing target cells and killed much more efficiently than an equivalent chimeric receptor system which lacked CD3 zeta endodomains.

Co-culture of PBMCs expressing the 4th generation CAR with ROR1-expressing target cells lead to significant levels of IFNγ release, unlike PBMCs expressing an equivalent chimeric receptor system which lacks CD3 zeta endodomains (FIG. 11).

Example 5—Generation of a 4th Generation CAR System with Antigen Binding Domains Against the Same Epitope of a Target Antigen A 4th generation CAR system was designed having scFvs which bind to the same epitope of the antigen ROR1 (FIG. 12). The first chimeric receptor had an antigen binding domain comprising an R12 scFv, a human Fc spacer, an IL2 receptor endodomain and a CD3 zeta endodomain; the second chimeric receptor had an antigen binding domain comprising an R12 scFv, a CD8 stalk spacer, an IL2 receptor γ endodomain and a CD3 zeta endodomain. The DNA sequence of the R12ScFv of the first chimeric receptor was wobbled to avoid homologous recombination. A control receptor system was also designed which lacked the cytokine receptor endodomains but which was otherwise identical (also shown in FIG. 12).

Example 6—A 4th Generation CAR System with Antigen Binding Domains Against the Same Epitope of a Target Antigen Shows Increased Proliferation/Survival than an Equivalent CAR System Lacking Cytokine Receptor Endodomains An equivalent survival/proliferation assay was conducted as described in Example 3 for the constructs developed in Example 5 and the results are shown in FIGS. 13 and 14. As shown in FIG. 13, the 4th generation CAR which included cytokine receptor and CD3 zeta endodomains showed a greater fold-enrichment in transduced cells when co-cultured with ligand for 3 days than an equivalent chimeric receptor system which lacked cytokine receptor endodomains. As shown in FIG. 8, the presence of ligand greatly increased cell survival/proliferation after three days of culture for cells expressing the 4th generation CAR, whereas the presence of ligand had little effect on the proliferation/survival of cells expressing an equivalent chimeric receptor system lacking cytokine receptor endodomains.

It is therefore possible to target an antigen using the chimeric receptor system of the present invention using two antigen binding domains which bind the same epitope of the target antigen. This potentially simplifies the design of the chimeric receptor system and avoids the need to find mutually exclusive epitopes for each target antigen.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A chimeric receptor system which comprises a first chimeric receptor and a second chimeric receptor, wherein the first and the second chimeric receptors each comprise:
- a ligand-binding exodomain that comprises an antigen binding domain of an antibody;
- a transmembrane domain; and
- an endodomain which comprises:
  - (i) a cytokine receptor endodomain; and
  - (ii) an intracellular T cell signalling domain,
- wherein the ligand is a tumour-secreted factor or a tumour cell surface antigen;
- wherein the cytokine receptor endodomain of the first chimeric receptor comprises or consists of IL-2 receptor β-chain endodomain or IL-7 receptor α-chain endodomain;
- wherein the cytokine receptor endodomain of the second chimeric receptor comprises or consists of common γ-chain receptor endodomain; and
- wherein the intracellular T cell signaling domain of the first chimeric receptor or the intracellular T cell signaling domain of the second chimeric receptor includes a CD3 zeta endodomain.

2. A chimeric receptor system according to claim 1, wherein the ligand-binding exodomain of the first chimeric receptor and the ligand-binding exodomain of the second chimeric receptor bind to different epitopes of the same antigen.

3. The chimeric receptor system according to claim 1, wherein the ligand-binding exodomain of the first chimeric receptor and the ligand-binding exodomain of the second chimeric receptor bind to the same epitope of the same antigen.

4. The chimeric receptor system according to claim 1, wherein the ligand-binding exodomain of the first chimeric receptor comprises a single-chain variable fragment (scFv) derived from a monoclonal antibody that binds the ligand, and the ligand-binding exodomain of the second chimeric receptor comprises an scFv derived from a monoclonal antibody that binds the ligand.

5. The chimeric receptor system according to claim 1, wherein the ligand-binding exodomain of either the first chimeric receptor or the second chimeric receptor comprises a $V_H$ domain of an antibody that binds the ligand, and the ligand-binding domain of the other chimeric receptor comprises the $V_L$ domain of the antibody that binds the ligand.

6. The chimeric receptor system according to claim 1, wherein the ligand-binding exodomain of the first chimeric receptor comprises a single domain binder, and the ligand-binding exodomain of the second chimeric receptor comprises a single domain binder.

7. The chimeric receptor system according to claim 1, wherein the ligand is CD19, CD20, or CD22.

8. The chimeric receptor system according to claim 1, wherein the ligand is ErbB2, MUC1, GD2, NCAM, ALK, GD2, Folate binding protein, CA-125, EGFR, Vimentin, Carbonic anhydrase IX, G250, PSCA, PSMA, or A33.

9. The chimeric receptor system according to claim 1, wherein the ligand is CD13, CD33, CD19, CD52, CD160, CDS, BCMA, or CD138.

10. A chimeric receptor system according to claim 1, wherein the intracellular T cell signalling domain of the first chimeric receptor or the intracellular T cell signaling domain of the second chimeric receptor comprises one or more of the following: CD28 endodomain, OX40 endodomain, 4-1 BB endodomain, CD2 endodomain, CD27 endodomain, ICOS endodomain, and CD40 endodomain.

11. The chimeric receptor system according to claim 1, wherein the arrangement of the intracellular T cell signalling domain(s) and the cytokine receptor endodomain of each chimeric receptor is such that when the receptor is expressed at the surface of a cell, the intracellular T cell signalling domain(s) is/are positioned distal to the membrane and the cytokine receptor endodomain is positioned proximal to the membrane on the intracellular cell surface.

12. The chimeric receptor system according to claim 1, wherein the first chimeric receptor comprises a CD3 zeta endodomain, and the second chimeric receptor comprises one or more co-stimulatory domain(s) selected from CD28 endodomain, OX40 endodomain and 4-1 BB endodomain.

13. The chimeric receptor system according to claim 1, wherein both the first and second chimeric receptors comprise CD3 zeta endodomains.

14. A cell which comprises a chimeric receptor system according to claim 1.

15. A nucleic acid construct comprising a nucleotide sequence encoding the first chimeric receptor according to claim 1 and comprising a nucleotide sequence encoding the second chimeric receptor according to claim 1.

16. A vector comprising a nucleic acid construct according to claim 15.

17. A kit of vectors for producing a chimeric receptor system according to claim 1, which comprises:
  i) a vector comprising a nucleic acid sequence encoding the first chimeric receptor; and
  ii) a vector comprising a nucleic acid sequence encoding the second chimeric receptor.

18. A method for making a cell, which comprises the step of introducing into the cell the nucleic acid construct of claim 15.

19. A pharmaceutical composition comprising a plurality of cells according to claim 14.

20. A method for treating a cancer, which comprises the step of administering a pharmaceutical composition according to claim 19 to a subject.

21. A method comprising:
  (i) isolating a T cell-containing sample from a subject;
  (ii) transducing or transfecting T cells from the sample with a nucleic acid construct according to claim 15, or a vector comprising said nucleic acid construct; and
  (iii) administering transformed or transfected cells from (ii) to the subject.

22. A chimeric receptor system comprising a chimeric receptor and an intracellular fusion protein,
  wherein the chimeric receptor comprises a ligand-binding exodomain that comprises an antigen binding domain of an antibody; a transmembrane domain; and an endodomain which comprises: (i) a cytokine receptor endodomain; and (ii) an intracellular T cell signalling domain, said intracellular T cell signaling domain comprising a CD3 zeta endodomain;

wherein the intracellular fusion protein comprises a cytokine receptor endodomain and a ZAP70 SH2 domain; and wherein the cytokine receptor endodomain of the chimeric receptor is complementary to the cytokine receptor endodomain of the intracellular fusion protein, one of said endodomains comprising or consisting of an IL-2 receptor β-chain endodomain or IL-7 receptor α-chain endodomain, and the other of said endodomains comprising or consisting of a common γ-chain receptor endodomain.

23. The chimeric receptor system according to claim 22, wherein the ligand is CD19, CD20, or CD22.

24. The chimeric receptor system according to claim 22, wherein the ligand is ErbB2, MUC1, GD2, NCAM, ALK, GD2, Folate binding protein, CA-125, EGFR, Vimentin, Carbonic anhydrase IX, G250, PSCA, PSMA, or A33.

25. The chimeric receptor system according to claim 22, wherein the ligand is CD13, CD33, CD19, CD52, CD160, CDS, BCMA, or CD138.

26. A cell which comprises a chimeric receptor system according to claim 22.

27. A pharmaceutical composition comprising a plurality of cells according to claim 26.

28. A method for treating a cancer, which comprises the step of administering a pharmaceutical composition according to claim 27 to a subject.

29. A chimeric receptor system comprising a chimeric receptor and a transmembrane protein, wherein the chimeric receptor comprises a ligand-binding exodomain that comprises an antigen binding domain of an antibody; a transmembrane domain; and an endodomain which comprises: (i) a cytokine receptor endodomain; and (ii) an intracellular T cell signalling domain, said intracellular T cell signaling domain comprising a CD3 zeta endodomain;

wherein the transmembrane protein lacks a ligand-binding exodomain, and comprises a cytokine receptor endodomain and a ZAP70 SH2 domain; and wherein the cytokine receptor endodomain of the chimeric receptor is complementary to the cytokine receptor endodomain of the transmembrane protein, one of said endodomains comprising or consisting of an IL-2 receptor β-chain endodomain or IL-7 receptor α-chain endodomain, and the other of said endodomains comprising or consisting of a common γ-chain receptor endodomain.

30. The chimeric receptor system according to claim 29, wherein the ligand is CD19, CD20, or CD22.

31. The chimeric receptor system according to claim 29, wherein the ligand is ErbB2, MUC1, GD2, NCAM, ALK, GD2, Folate binding protein, CA-125, EGFR, Vimentin, Carbonic anhydrase IX, G250, PSCA, PSMA, or A33.

32. The chimeric receptor system according to claim 29, wherein the ligand is CD13, CD33, CD19, CD52, CD160, CD5, BCMA, or CD138.

33. A cell which comprises a chimeric receptor system according to claim 29.

34. A pharmaceutical composition comprising a plurality of cells according to claim 33.

35. A method for treating a cancer, which comprises the step of administering a pharmaceutical composition according to claim 34 to a subject.

\* \* \* \* \*

UNITED STATES PATENT AND TRADEMARK OFFICE
CERTIFICATE OF CORRECTION

PATENT NO. : 11,242,377 B2
APPLICATION NO. : 15/770110
DATED : February 8, 2022
INVENTOR(S) : Martin Pulé et al.

It is certified that error appears in the above-identified patent and that said Letters Patent is hereby corrected as shown below:

In the Claims

At Column 58, Line 11, "CDS," should be -- CD5, --.

At Column 58, Lines 16-17, "4-1 BB" should be -- 4-1BB --.

At Column 58, Line 31, "4-1 BB" should be -- 4-1BB --.

At Column 59, Line 25, "CDS," should be -- CD5, --.

Signed and Sealed this
Fifth Day of September, 2023

Katherine Kelly Vidal
*Director of the United States Patent and Trademark Office*

SEQUENCE LISTING

```
<160> NUMBER OF SEQ ID NOS: 27

<210> SEQ ID NO 1
<211> LENGTH: 86
<212> TYPE: PRT
<213> ORGANISM: Artificial Sequence
<220> FEATURE:
```

<223> OTHER INFORMATION: endodomain derived from human common gamma
      chain

<400> SEQUENCE: 1

Glu Arg Thr Met Pro Arg Ile Pro Thr Leu Lys Asn Leu Glu Asp Leu
1               5                   10                  15

Val Thr Glu Tyr His Gly Asn Phe Ser Ala Trp Ser Gly Val Ser Lys
            20                  25                  30

Gly Leu Ala Glu Ser Leu Gln Pro Asp Tyr Ser Glu Arg Leu Cys Leu
        35                  40                  45

Val Ser Glu Ile Pro Pro Lys Gly Gly Ala Leu Gly Glu Gly Pro Gly
50                  55                  60

Ala Ser Pro Cys Asn Gln His Ser Pro Tyr Trp Ala Pro Pro Cys Tyr
65                  70                  75                  80

Thr Leu Lys Pro Glu Thr
                85

<210> SEQ ID NO 2
<211> LENGTH: 286
<212> TYPE: PRT
<213> ORGANISM: Artificial Sequence
<220> FEATURE:
<223> OTHER INFORMATION: endodomain derived from human IL-2Rbeta

<400> SEQUENCE: 2

Asn Cys Arg Asn Thr Gly Pro Trp Leu Lys Lys Val Leu Lys Cys Asn
1               5                   10                  15

Thr Pro Asp Pro Ser Lys Phe Phe Ser Gln Leu Ser Ser Glu His Gly
            20                  25                  30

Gly Asp Val Gln Lys Trp Leu Ser Ser Pro Phe Pro Ser Ser Ser Phe
        35                  40                  45

Ser Pro Gly Gly Leu Ala Pro Glu Ile Ser Pro Leu Glu Val Leu Glu
    50                  55                  60

Arg Asp Lys Val Thr Gln Leu Leu Leu Gln Gln Asp Lys Val Pro Glu
65                  70                  75                  80

Pro Ala Ser Leu Ser Ser Asn His Ser Leu Thr Ser Cys Phe Thr Asn
                85                  90                  95

Gln Gly Tyr Phe Phe Phe His Leu Pro Asp Ala Leu Glu Ile Glu Ala
            100                 105                 110

Cys Gln Val Tyr Phe Thr Tyr Asp Pro Tyr Ser Glu Glu Asp Pro Asp
        115                 120                 125

Glu Gly Val Ala Gly Ala Pro Thr Gly Ser Ser Pro Gln Pro Leu Gln
    130                 135                 140

Pro Leu Ser Gly Glu Asp Asp Ala Tyr Cys Thr Phe Pro Ser Arg Asp
145                 150                 155                 160

Asp Leu Leu Leu Phe Ser Pro Ser Leu Leu Gly Gly Pro Ser Pro Pro
                165                 170                 175

Ser Thr Ala Pro Gly Gly Ser Gly Ala Gly Glu Glu Arg Met Pro Pro
            180                 185                 190

Ser Leu Gln Glu Arg Val Pro Arg Asp Trp Asp Pro Gln Pro Leu Gly
        195                 200                 205

Pro Pro Thr Pro Gly Val Pro Asp Leu Val Asp Phe Gln Pro Pro Pro
    210                 215                 220

Glu Leu Val Leu Arg Glu Ala Gly Glu Glu Val Pro Asp Ala Gly Pro
225                 230                 235                 240

Arg Glu Gly Val Ser Phe Pro Trp Ser Arg Pro Pro Gly Gln Gly Glu

```
                        245                 250                 255
Phe Arg Ala Leu Asn Ala Arg Leu Pro Leu Asn Thr Asp Ala Tyr Leu
                260                 265                 270

Ser Leu Gln Glu Leu Gln Gly Gln Asp Pro Thr His Leu Val
            275                 280                 285

<210> SEQ ID NO 3
<211> LENGTH: 195
<212> TYPE: PRT
<213> ORGANISM: Artificial Sequence
<220> FEATURE:
<223> OTHER INFORMATION: endodomain derived from human IL-7Ralpha

<400> SEQUENCE: 3

Lys Lys Arg Ile Lys Pro Ile Val Trp Pro Ser Leu Pro Asp His Lys
1               5                   10                  15

Lys Thr Leu Glu His Leu Cys Lys Lys Pro Arg Lys Asn Leu Asn Val
            20                  25                  30

Ser Phe Asn Pro Glu Ser Phe Leu Asp Cys Gln Ile His Arg Val Asp
        35                  40                  45

Asp Ile Gln Ala Arg Asp Glu Val Glu Gly Phe Leu Gln Asp Thr Phe
    50                  55                  60

Pro Gln Gln Leu Glu Glu Ser Glu Lys Gln Arg Leu Gly Gly Asp Val
65                  70                  75                  80

Gln Ser Pro Asn Cys Pro Ser Glu Asp Val Val Ile Thr Pro Glu Ser
                85                  90                  95

Phe Gly Arg Asp Ser Ser Leu Thr Cys Leu Ala Gly Asn Val Ser Ala
            100                 105                 110

Cys Asp Ala Pro Ile Leu Ser Ser Ser Arg Ser Leu Asp Cys Arg Glu
        115                 120                 125

Ser Gly Lys Asn Gly Pro His Val Tyr Gln Asp Leu Leu Leu Ser Leu
    130                 135                 140

Gly Thr Thr Asn Ser Thr Leu Pro Pro Pro Phe Ser Leu Gln Ser Gly
145                 150                 155                 160

Ile Leu Thr Leu Asn Pro Val Ala Gln Gly Gln Pro Ile Leu Thr Ser
                165                 170                 175

Leu Gly Ser Asn Gln Glu Glu Ala Tyr Val Thr Met Ser Ser Phe Tyr
            180                 185                 190

Gln Asn Gln
        195

<210> SEQ ID NO 4
<211> LENGTH: 234
<212> TYPE: PRT
<213> ORGANISM: Artificial Sequence
<220> FEATURE:
<223> OTHER INFORMATION: hinge-CH2CH3 of human IgG1

<400> SEQUENCE: 4

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Val Val
        35                  40                  45

Val Asp Val Ser His Glu Asp Pro Glu Val Lys Phe Asn Trp Tyr Val
    50                  55                  60
```

```
Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Lys Asp
225                 230

<210> SEQ ID NO 5
<211> LENGTH: 46
<212> TYPE: PRT
<213> ORGANISM: Artificial Sequence
<220> FEATURE:
<223> OTHER INFORMATION: human CD8 stalk

<400> SEQUENCE: 5

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile
        35                  40                  45

<210> SEQ ID NO 6
<211> LENGTH: 20
<212> TYPE: PRT
<213> ORGANISM: Artificial Sequence
<220> FEATURE:
<223> OTHER INFORMATION: human IgG1 hinge

<400> SEQUENCE: 6

Ala Glu Pro Lys Ser Pro Asp Lys Thr His Thr Cys Pro Pro Cys Pro
1               5                   10                  15

Lys Asp Pro Lys
            20

<210> SEQ ID NO 7
<211> LENGTH: 21
<212> TYPE: PRT
<213> ORGANISM: Artificial Sequence
<220> FEATURE:
<223> OTHER INFORMATION: transmembrane derived from human common gamma
      chain

<400> SEQUENCE: 7
```

```
Val Val Ile Ser Val Gly Ser Met Gly Leu Ile Ile Ser Leu Leu Cys
1               5                   10                  15

Val Tyr Phe Trp Leu
            20
```

<210> SEQ ID NO 8
<211> LENGTH: 25
<212> TYPE: PRT
<213> ORGANISM: Artificial Sequence
<220> FEATURE:
<223> OTHER INFORMATION: transmembrane derived from human IL-2Rbeta

<400> SEQUENCE: 8

```
Ile Pro Trp Leu Gly His Leu Leu Val Gly Leu Ser Gly Ala Phe Gly
1               5                   10                  15

Phe Ile Ile Leu Val Tyr Leu Leu Ile
            20                  25
```

<210> SEQ ID NO 9
<211> LENGTH: 25
<212> TYPE: PRT
<213> ORGANISM: Artificial Sequence
<220> FEATURE:
<223> OTHER INFORMATION: transmembrane derived from human IL-7Ralpha

<400> SEQUENCE: 9

```
Pro Ile Leu Leu Thr Ile Ser Ile Leu Ser Phe Phe Ser Val Ala Leu
1               5                   10                  15

Leu Val Ile Leu Ala Cys Val Leu Trp
            20                  25
```

<210> SEQ ID NO 10
<211> LENGTH: 22
<212> TYPE: PRT
<213> ORGANISM: Artificial Sequence
<220> FEATURE:
<223> OTHER INFORMATION: transmembrane derived from human IL-15Ralpha

<400> SEQUENCE: 10

```
Ala Ile Ser Thr Ser Thr Val Leu Leu Cys Gly Leu Ser Ala Val Ser
1               5                   10                  15

Leu Leu Ala Cys Tyr Leu
            20
```

<210> SEQ ID NO 11
<211> LENGTH: 238
<212> TYPE: PRT
<213> ORGANISM: Artificial Sequence
<220> FEATURE:
<223> OTHER INFORMATION: scFv based on J591

<400> SEQUENCE: 11

```
Glu Val Gln Leu Gln Gln Ser Gly Pro Glu Leu Lys Lys Pro Gly Thr
1               5                   10                  15

Ser Val Arg Ile Ser Cys Lys Thr Ser Gly Tyr Thr Phe Thr Glu Tyr
            20                  25                  30

Thr Ile His Trp Val Lys Gln Ser His Gly Lys Ser Leu Glu Trp Ile
        35                  40                  45

Gly Asn Ile Asn Pro Asn Asn Gly Gly Thr Thr Tyr Asn Gln Lys Phe
    50                  55                  60

Glu Asp Lys Ala Thr Leu Thr Val Asp Lys Ser Ser Ser Thr Ala Tyr
65                  70                  75                  80
```

```
Met Glu Leu Arg Ser Leu Thr Ser Glu Asp Ser Ala Val Tyr Tyr Cys
                85                  90                  95

Ala Ala Gly Trp Asn Phe Asp Tyr Trp Gly Gln Gly Thr Thr Leu Thr
            100                 105                 110

Val Ser Ser Gly Gly Gly Gly Ser Gly Gly Gly Gly Ser Gly Gly Gly
        115                 120                 125

Gly Ser Asp Ile Val Met Thr Gln Ser His Lys Phe Met Ser Thr Ser
    130                 135                 140

Val Gly Asp Arg Val Ser Ile Ile Cys Lys Ala Ser Gln Asp Val Gly
145                 150                 155                 160

Thr Ala Val Asp Trp Tyr Gln Gln Lys Pro Gly Gln Ser Pro Lys Leu
                165                 170                 175

Leu Ile Tyr Trp Ala Ser Thr Arg His Thr Gly Val Pro Asp Arg Phe
            180                 185                 190

Thr Gly Ser Gly Ser Gly Thr Asp Phe Thr Leu Thr Ile Thr Asn Val
        195                 200                 205

Gln Ser Glu Asp Leu Ala Asp Tyr Phe Cys Gln Gln Tyr Asn Ser Tyr
    210                 215                 220

Pro Leu Thr Phe Gly Ala Gly Thr Met Leu Asp Leu Lys Arg
225                 230                 235

<210> SEQ ID NO 12
<211> LENGTH: 112
<212> TYPE: PRT
<213> ORGANISM: Artificial Sequence
<220> FEATURE:
<223> OTHER INFORMATION: CD3 Z endodomain

<400> SEQUENCE: 12

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 13
<211> LENGTH: 152
<212> TYPE: PRT
<213> ORGANISM: Artificial Sequence
<220> FEATURE:
<223> OTHER INFORMATION: CD28 and CD3 Zeta endodomains

<400> SEQUENCE: 13

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser Arg Val Lys Phe Ser Arg Ser Ala
        35                  40                  45
```

Asp Ala Pro Ala Tyr Gln Gln Gly Gln Asn Gln Leu Tyr Asn Glu Leu
                50                  55                  60

Asn Leu Gly Arg Arg Glu Tyr Asp Val Leu Asp Lys Arg Arg Gly
 65                  70                  75                  80

Arg Asp Pro Glu Met Gly Gly Lys Pro Arg Arg Lys Asn Pro Gln Glu
                    85                  90                  95

Gly Leu Tyr Asn Glu Leu Gln Lys Asp Lys Met Ala Glu Ala Tyr Ser
                100                 105                 110

Glu Ile Gly Met Lys Gly Glu Arg Arg Arg Gly Lys Gly His Asp Gly
            115                 120                 125

Leu Tyr Gln Gly Leu Ser Thr Ala Thr Lys Asp Thr Tyr Asp Ala Leu
        130                 135                 140

His Met Gln Ala Leu Pro Pro Arg
145                 150

<210> SEQ ID NO 14
<211> LENGTH: 188
<212> TYPE: PRT
<213> ORGANISM: Artificial Sequence
<220> FEATURE:
<223> OTHER INFORMATION: CD28, OX40 and CD3 Zeta endodomains

<400> SEQUENCE: 14

Ser Lys Arg Ser Arg Leu Leu His Ser Asp Tyr Met Asn Met Thr Pro
 1               5                  10                  15

Arg Arg Pro Gly Pro Thr Arg Lys His Tyr Gln Pro Tyr Ala Pro Pro
                20                  25                  30

Arg Asp Phe Ala Ala Tyr Arg Ser Arg Asp Gln Arg Leu Pro Pro Asp
            35                  40                  45

Ala His Lys Pro Pro Gly Gly Gly Ser Phe Arg Thr Pro Ile Gln Glu
        50                  55                  60

Glu Gln Ala Asp Ala His Ser Thr Leu Ala Lys Ile Arg Val Lys Phe
 65                  70                  75                  80

Ser Arg Ser Ala Asp Ala Pro Ala Tyr Gln Gln Gly Gln Asn Gln Leu
                85                  90                  95

Tyr Asn Glu Leu Asn Leu Gly Arg Arg Glu Glu Tyr Asp Val Leu Asp
                100                 105                 110

Lys Arg Arg Gly Arg Asp Pro Glu Met Gly Gly Lys Pro Arg Arg Lys
            115                 120                 125

Asn Pro Gln Glu Gly Leu Tyr Asn Glu Leu Gln Lys Asp Lys Met Ala
        130                 135                 140

Glu Ala Tyr Ser Glu Ile Gly Met Lys Gly Glu Arg Arg Arg Gly Lys
145                 150                 155                 160

Gly His Asp Gly Leu Tyr Gln Gly Leu Ser Thr Ala Thr Lys Asp Thr
                165                 170                 175

Tyr Asp Ala Leu His Met Gln Ala Leu Pro Pro Arg
                180                 185

<210> SEQ ID NO 15
<211> LENGTH: 38
<212> TYPE: PRT
<213> ORGANISM: Artificial Sequence
<220> FEATURE:
<223> OTHER INFORMATION: ICOS endodomain

<400> SEQUENCE: 15

Cys Trp Leu Thr Lys Lys Lys Tyr Ser Ser Ser Val His Asp Pro Asn

```
                1               5                  10                 15
Gly Glu Tyr Met Phe Met Arg Ala Val Asn Thr Ala Lys Lys Ser Arg
                20                 25                 30

Leu Thr Asp Val Thr Leu
            35

<210> SEQ ID NO 16
<211> LENGTH: 48
<212> TYPE: PRT
<213> ORGANISM: Artificial Sequence
<220> FEATURE:
<223> OTHER INFORMATION: CD27 endodomain

<400> SEQUENCE: 16

Gln Arg Arg Lys Tyr Arg Ser Asn Lys Gly Glu Ser Pro Val Glu Pro
1               5                  10                 15

Ala Glu Pro Cys His Tyr Ser Cys Pro Arg Glu Glu Glu Gly Ser Thr
                20                 25                 30

Ile Pro Ile Gln Glu Asp Tyr Arg Lys Pro Glu Pro Ala Cys Ser Pro
            35                 40                 45

<210> SEQ ID NO 17
<211> LENGTH: 111
<212> TYPE: PRT
<213> ORGANISM: Artificial Sequence
<220> FEATURE:
<223> OTHER INFORMATION: BTLA endodomain

<400> SEQUENCE: 17

Arg Arg His Gln Gly Lys Gln Asn Glu Leu Ser Asp Thr Ala Gly Arg
1               5                  10                 15

Glu Ile Asn Leu Val Asp Ala His Leu Lys Ser Glu Gln Thr Glu Ala
                20                 25                 30

Ser Thr Arg Gln Asn Ser Gln Val Leu Leu Ser Glu Thr Gly Ile Tyr
            35                 40                 45

Asp Asn Asp Pro Asp Leu Cys Phe Arg Met Gln Glu Gly Ser Glu Val
        50                 55                 60

Tyr Ser Asn Pro Cys Leu Glu Glu Asn Lys Pro Gly Ile Val Tyr Ala
65                  70                 75                 80

Ser Leu Asn His Ser Val Ile Gly Pro Asn Ser Arg Leu Ala Arg Asn
                85                 90                 95

Val Lys Glu Ala Pro Thr Glu Tyr Ala Ser Ile Cys Val Arg Ser
            100                105                110

<210> SEQ ID NO 18
<211> LENGTH: 188
<212> TYPE: PRT
<213> ORGANISM: Artificial Sequence
<220> FEATURE:
<223> OTHER INFORMATION: CD30 endodomain

<400> SEQUENCE: 18

His Arg Arg Ala Cys Arg Lys Arg Ile Arg Gln Lys Leu His Leu Cys
1               5                  10                 15

Tyr Pro Val Gln Thr Ser Gln Pro Lys Leu Glu Leu Val Asp Ser Arg
                20                 25                 30

Pro Arg Arg Ser Ser Thr Gln Leu Arg Ser Gly Ala Ser Val Thr Glu
            35                 40                 45

Pro Val Ala Glu Glu Arg Gly Leu Met Ser Gln Pro Leu Met Glu Thr
        50                 55                 60
```

```
Cys His Ser Val Gly Ala Ala Tyr Leu Glu Ser Leu Pro Leu Gln Asp
 65                  70                  75                  80

Ala Ser Pro Ala Gly Pro Ser Ser Pro Arg Asp Leu Pro Glu Pro
             85                  90                  95

Arg Val Ser Thr Glu His Thr Asn Asn Lys Ile Glu Lys Ile Tyr Ile
            100                 105                 110

Met Lys Ala Asp Thr Val Ile Val Gly Thr Val Lys Ala Glu Leu Pro
        115                 120                 125

Glu Gly Arg Gly Leu Ala Gly Pro Ala Glu Pro Glu Leu Glu Glu Glu
    130                 135                 140

Leu Glu Ala Asp His Thr Pro His Tyr Pro Glu Gln Glu Thr Glu Pro
145                 150                 155                 160

Pro Leu Gly Ser Cys Ser Asp Val Met Leu Ser Val Glu Glu Glu Gly
                165                 170                 175

Lys Glu Asp Pro Leu Pro Thr Ala Ala Ser Gly Lys
            180                 185
```

<210> SEQ ID NO 19
<211> LENGTH: 58
<212> TYPE: PRT
<213> ORGANISM: Artificial Sequence
<220> FEATURE:
<223> OTHER INFORMATION: GITR endodomain

<400> SEQUENCE: 19

```
Gln Leu Gly Leu His Ile Trp Gln Leu Arg Ser Gln Cys Met Trp Pro
 1               5                  10                  15

Arg Glu Thr Gln Leu Leu Leu Glu Val Pro Pro Ser Thr Glu Asp Ala
            20                  25                  30

Arg Ser Cys Gln Phe Pro Glu Glu Glu Arg Gly Glu Arg Ser Ala Glu
        35                  40                  45

Glu Lys Gly Arg Leu Gly Asp Leu Trp Val
    50                  55
```

<210> SEQ ID NO 20
<211> LENGTH: 60
<212> TYPE: PRT
<213> ORGANISM: Artificial Sequence
<220> FEATURE:
<223> OTHER INFORMATION: HVEM endodomain

<400> SEQUENCE: 20

```
Cys Val Lys Arg Arg Lys Pro Arg Gly Asp Val Val Lys Val Ile Val
 1               5                  10                  15

Ser Val Gln Arg Lys Arg Gln Glu Ala Glu Gly Glu Ala Thr Val Ile
            20                  25                  30

Glu Ala Leu Gln Ala Pro Pro Asp Val Thr Thr Val Ala Val Glu Glu
        35                  40                  45

Thr Ile Pro Ser Phe Thr Gly Arg Ser Pro Asn His
    50                  55                  60
```

<210> SEQ ID NO 21
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 21

```
Arg Ala Glu Gly Arg Gly Ser Leu Leu Thr Cys Gly Asp Val Glu Glu
1               5                   10                  15

Asn Pro Gly Pro
            20
```

<210> SEQ ID NO 22
<211> LENGTH: 619
<212> TYPE: PRT
<213> ORGANISM: Homo sapiens

<400> SEQUENCE: 22

```
Met Pro Asp Pro Ala Ala His Leu Pro Phe Phe Tyr Gly Ser Ile Ser
1               5                   10                  15

Arg Ala Glu Ala Glu His Leu Lys Leu Ala Gly Met Ala Asp Gly
                20                  25                  30

Leu Phe Leu Leu Arg Gln Cys Leu Arg Ser Leu Gly Gly Tyr Val Leu
            35                  40                  45

Ser Leu Val His Asp Val Arg Phe His His Phe Pro Ile Glu Arg Gln
        50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
130                 135                 140

Gln Ala Pro Gln Val Glu Lys Leu Ile Ala Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Pro Thr Leu Pro Ala
            260                 265                 270

His Pro Ser Thr Leu Thr His Pro Gln Arg Arg Ile Asp Thr Leu Asn
        275                 280                 285

Ser Asp Gly Tyr Thr Pro Glu Pro Ala Arg Ile Thr Ser Pro Asp Lys
290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Lys Leu Phe Leu Lys Arg Asp Asn
                325                 330                 335

Leu Leu Ile Ala Asp Ile Glu Leu Gly Cys Gly Asn Phe Gly Ser Val
            340                 345                 350
```

```
Arg Gln Gly Val Tyr Arg Met Arg Lys Lys Gln Ile Asp Val Ala Ile
            355                 360                 365
Lys Val Leu Lys Gln Gly Thr Glu Lys Ala Asp Thr Glu Glu Met Met
    370                 375                 380
Arg Glu Ala Gln Ile Met His Gln Leu Asp Asn Pro Tyr Ile Val Arg
385                 390                 395                 400
Leu Ile Gly Val Cys Gln Ala Glu Ala Leu Met Leu Val Met Glu Met
                405                 410                 415
Ala Gly Gly Gly Pro Leu His Lys Phe Leu Val Gly Lys Arg Glu Glu
            420                 425                 430
Ile Pro Val Ser Asn Val Ala Glu Leu Leu His Gln Val Ser Met Gly
            435                 440                 445
Met Lys Tyr Leu Glu Glu Lys Asn Phe Val His Arg Asp Leu Ala Ala
    450                 455                 460
Arg Asn Val Leu Leu Val Asn Arg His Tyr Ala Lys Ile Ser Asp Phe
465                 470                 475                 480
Gly Leu Ser Lys Ala Leu Gly Ala Asp Asp Ser Tyr Tyr Thr Ala Arg
                485                 490                 495
Ser Ala Gly Lys Trp Pro Leu Lys Trp Tyr Ala Pro Glu Cys Ile Asn
            500                 505                 510
Phe Arg Lys Phe Ser Ser Arg Ser Asp Val Trp Ser Tyr Gly Val Thr
            515                 520                 525
Met Trp Glu Ala Leu Ser Tyr Gly Gln Lys Pro Tyr Lys Lys Met Lys
    530                 535                 540
Gly Pro Glu Val Met Ala Phe Ile Glu Gln Gly Lys Arg Met Glu Cys
545                 550                 555                 560
Pro Pro Glu Cys Pro Pro Glu Leu Tyr Ala Leu Met Ser Asp Cys Trp
                565                 570                 575
Ile Tyr Lys Trp Glu Asp Arg Pro Asp Phe Leu Thr Val Glu Gln Arg
            580                 585                 590
Met Arg Ala Cys Tyr Tyr Ser Leu Ala Ser Lys Val Glu Gly Pro Pro
            595                 600                 605
Gly Ser Thr Gln Lys Ala Glu Ala Ala Cys Ala
    610                 615

<210> SEQ ID NO 23
<211> LENGTH: 280
<212> TYPE: PRT
<213> ORGANISM: Artificial Sequence
<220> FEATURE:
<223> OTHER INFORMATION: ZAP70 SH2 domain

<400> SEQUENCE: 23

Met Pro Asp Pro Ala Ala His Leu Pro Phe Phe Tyr Gly Ser Ile Ser
1               5                   10                  15
Arg Ala Glu Ala Glu Glu His Leu Lys Leu Ala Gly Met Ala Asp Gly
            20                  25                  30
Leu Phe Leu Leu Arg Gln Cys Leu Arg Ser Leu Gly Gly Tyr Val Leu
        35                  40                  45
Ser Leu Val His Asp Val Arg Phe His His Phe Pro Ile Glu Arg Gln
    50                  55                  60
Leu Asn Gly Thr Tyr Ala Ile Ala Gly Gly Lys Ala His Cys Gly Pro
65                  70                  75                  80
Ala Glu Leu Cys Glu Phe Tyr Ser Arg Asp Pro Asp Gly Leu Pro Cys
                85                  90                  95
```

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
                195                 200                 205

Tyr His Tyr Leu Ile Ser Gln Asp Lys Ala Gly Lys Tyr Cys Ile Pro
            210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Ala Pro Thr Leu Pro Ala
            260                 265                 270

His Pro Ser Thr Leu Thr His Pro
            275                 280

<210> SEQ ID NO 24
<211> LENGTH: 5
<212> TYPE: PRT
<213> ORGANISM: Artificial Sequence
<220> FEATURE:
<223> OTHER INFORMATION: Type I cytokine receptor motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 24

Trp Ser Xaa Trp Ser
1               5

<210> SEQ ID NO 25
<211> LENGTH: 4
<212> TYPE: PRT
<213> ORGANISM: Artificial Sequence
<220> FEATURE:
<223> OTHER INFORMATION: furin cleavage site
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be Arg or Lys

<400> SEQUENCE: 25

Arg Xaa Xaa Arg
1

<210> SEQ ID NO 26
<211> LENGTH: 7
<212> TYPE: PRT

<213> ORGANISM: Artificial Sequence
<220> FEATURE:
<223> OTHER INFORMATION: consensus Tobacco Etch Virus (TEV) cleavage site

<400> SEQUENCE: 26

```
Glu Asn Leu Tyr Phe Gln Ser
1               5
```

<210> SEQ ID NO 27
<211> LENGTH: 1166
<212> TYPE: PRT
<213> ORGANISM: Artificial Sequence
<220> FEATURE:
<223> OTHER INFORMATION: amino acid sequence for a dual CR system

<400> SEQUENCE: 27

```
Leu Pro Val Thr Ala Leu Leu Pro Leu Ala Leu Leu Leu His Ala
1               5                   10                  15

Ala Arg Pro Asp Ile Val Met Thr Gln Ser Pro Ala Thr Leu Ser Val
                20                  25                  30

Ser Pro Gly Glu Arg Ala Thr Leu Ser Cys Arg Ser Ser Gln Ser Leu
            35                  40                  45

Val His Ser Asn Gly Asn Thr Tyr Leu His Trp Tyr Gln Gln Lys Pro
50                  55                  60

Gly Gln Ala Pro Arg Leu Leu Ile Tyr Lys Val Ser Asn Arg Phe Ser
65                  70                  75                  80

Gly Val Pro Ala Arg Phe Ser Gly Ser Gly Ser Gly Ala Glu Phe Thr
                85                  90                  95

Leu Thr Ile Ser Ser Leu Gln Ser Glu Asp Phe Ala Val Tyr Tyr Cys
            100                 105                 110

Ser Gln Ser Thr His Val Pro Trp Thr Phe Gly Gln Gly Thr Arg Leu
        115                 120                 125

Glu Ile Lys Arg Ser Gly Gly Gly Gly Ser Gly Gly Gly Ser Gly
130                 135                 140

Gly Gly Gly Ser Glu Val Gln Leu Val Glu Ser Gly Ala Glu Val Lys
145                 150                 155                 160

Lys Pro Gly Ser Ser Val Lys Val Ser Cys Lys Ala Ser Gly Tyr Thr
                165                 170                 175

Phe Thr Asn Tyr Trp Ile Asn Trp Val Arg Gln Ala Pro Gly Gln Gly
            180                 185                 190

Leu Glu Trp Met Gly Asn Ile Tyr Pro Ser Asp Ser Phe Thr Asn Tyr
        195                 200                 205

Asn Gln Lys Phe Lys Asp Arg Val Thr Ile Thr Ala Asp Lys Ser Thr
    210                 215                 220

Ser Thr Val Tyr Leu Glu Leu Arg Asn Leu Arg Ser Asp Asp Thr Ala
225                 230                 235                 240

Val Tyr Tyr Cys Thr Arg Asp Thr Gln Glu Arg Ser Trp Tyr Phe Asp
                245                 250                 255

Val Trp Gly Gln Gly Thr Leu Val Thr Val Ser Asp Pro Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Phe Trp Val Val Ile
305                 310                 315                 320
```

-continued

Ser Val Gly Ser Met Gly Leu Ile Ile Ser Leu Leu Cys Val Tyr Phe
            325                 330                 335

Trp Leu Glu Arg Thr Met Pro Arg Ile Pro Thr Leu Lys Asn Leu Glu
            340                 345                 350

Asp Leu Val Thr Glu Tyr His Gly Asn Phe Ser Ala Trp Ser Gly Val
            355                 360                 365

Ser Lys Gly Leu Ala Glu Ser Leu Gln Pro Asp Tyr Ser Glu Arg Leu
            370                 375                 380

Cys Leu Val Ser Glu Ile Pro Pro Lys Gly Ala Leu Gly Glu Gly
385                 390                 395                 400

Pro Gly Ala Ser Pro Cys Asn Gln His Ser Pro Tyr Trp Ala Pro Pro
                    405                 410                 415

Cys Tyr Thr Leu Lys Pro Glu Thr Arg Arg Val Lys Phe Ser Arg Ser
                420                 425                 430

Ala Asp Ala Pro Ala Tyr Gln Gln Gly Gln Asn Gln Leu Tyr Asn Glu
            435                 440                 445

Leu Asn Leu Gly Arg Arg Glu Glu Tyr Asp Val Leu Asp Lys Arg Arg
            450                 455                 460

Gly Arg Asp Pro Glu Met Gly Gly Lys Pro Arg Arg Lys Asn Pro Gln
465                 470                 475                 480

Glu Gly Leu Tyr Asn Glu Leu Gln Lys Asp Lys Met Ala Glu Ala Tyr
                485                 490                 495

Ser Glu Ile Gly Met Lys Gly Glu Arg Arg Arg Gly Lys Gly His Asp
                500                 505                 510

Gly Leu Tyr Gln Gly Leu Ser Thr Ala Thr Lys Asp Thr Tyr Asp Ala
            515                 520                 525

Leu His Met Gln Ala Leu Pro Pro Arg Arg Ala Glu Gly Arg Gly Ser
            530                 535                 540

Leu Leu Thr Cys Gly Asp Val Glu Glu Asn Pro Gly Pro Leu Pro Val
545                 550                 555                 560

Thr Ala Leu Leu Leu Pro Leu Ala Leu Leu Leu His Ala Ala Arg Pro
                565                 570                 575

Glu Val Gln Leu Val Glu Ser Gly Gly Gly Leu Val Gln Pro Gly Gly
            580                 585                 590

Ser Leu Arg Leu Ser Cys Ala Ala Ser Gly Phe Ala Phe Ser Ile Tyr
            595                 600                 605

Asp Met Ser Trp Val Arg Gln Val Pro Gly Lys Gly Leu Glu Trp Val
            610                 615                 620

Ser Tyr Ile Ser Ser Gly Gly Gly Thr Thr Tyr Tyr Pro Asp Thr Val
625                 630                 635                 640

Lys Gly Arg Phe Thr Ile Ser Arg Asp Asn Ser Arg Asn Thr Leu Asp
                645                 650                 655

Leu Gln Met Asn Ser Leu Arg Val Glu Asp Thr Ala Val Tyr Tyr Cys
            660                 665                 670

Ala Arg His Ser Gly Tyr Gly Ser Ser Tyr Gly Val Leu Phe Ala Tyr
            675                 680                 685

Trp Gly Gln Gly Thr Leu Val Thr Val Ser Ser Gly Gly Gly Gly Ser
            690                 695                 700

Gly Gly Gly Gly Ser Gly Gly Gly Ser Asp Ile Gln Met Thr Gln
705                 710                 715                 720

Ser Pro Ser Ser Leu Ser Ala Ser Val Gly Asp Arg Val Thr Ile Thr
                725                 730                 735

```
Cys Arg Ala Ser Gln Asp Ile Ser Asn Tyr Leu Asn Trp Leu Gln Gln
                740                 745                 750

Lys Pro Gly Lys Ala Pro Lys Leu Leu Ile Tyr Tyr Thr Ser Ile Leu
                755                 760                 765

His Ser Gly Val Pro Ser Arg Phe Ser Gly Ser Gly Ser Gly Thr Glu
                770                 775                 780

Phe Thr Leu Thr Ile Ser Ser Leu Gln Pro Glu Asp Phe Ala Thr Tyr
785                 790                 795                 800

Tyr Cys Gln Gln Gly Asn Thr Leu Pro Trp Thr Phe Gly Gln Gly Thr
                805                 810                 815

Lys Leu Glu Ile Lys Arg Ser Pro Ala Glu Pro Lys Ser Pro Asp Lys
                820                 825                 830

Thr His Thr Cys Pro Pro Cys Pro Lys Asp Pro Lys Ala Cys Asp Ile
                835                 840                 845

Tyr Ile Trp Ala Pro Leu Ala Gly Thr Cys Gly Leu Gly His Leu Leu
                850                 855                 860

Val Gly Leu Ser Gly Ala Phe Gly Phe Ile Ile Leu Val Tyr Leu Leu
865                 870                 875                 880

Ile Asn Cys Arg Asn Thr Gly Pro Trp Leu Lys Lys Val Leu Lys Cys
                885                 890                 895

Asn Thr Pro Asp Pro Ser Lys Phe Phe Ser Gln Leu Ser Ser Glu His
                900                 905                 910

Gly Gly Asp Val Gln Lys Trp Leu Ser Ser Pro Phe Pro Ser Ser Ser
                915                 920                 925

Phe Ser Pro Gly Gly Leu Ala Pro Glu Ile Ser Pro Leu Glu Val Leu
                930                 935                 940

Glu Arg Asp Lys Val Thr Gln Leu Leu Leu Gln Gln Asp Lys Val Pro
945                 950                 955                 960

Glu Pro Ala Ser Leu Ser Ser Asn His Ser Leu Thr Ser Cys Phe Thr
                965                 970                 975

Asn Gln Gly Tyr Phe Phe Phe His Leu Pro Asp Ala Leu Glu Ile Glu
                980                 985                 990

Ala Cys Gln Val Tyr Phe Thr Tyr Asp Pro Tyr Ser Glu Glu Asp Pro
                995                 1000                1005

Asp Glu Gly Val Ala Gly Ala Pro Thr Gly Ser Ser Pro Gln Pro
        1010                1015                1020

Leu Gln Pro Leu Ser Gly Glu Asp Asp Ala Tyr Cys Thr Phe Pro
        1025                1030                1035

Ser Arg Asp Asp Leu Leu Leu Phe Ser Pro Ser Leu Leu Gly Gly
        1040                1045                1050

Pro Ser Pro Pro Ser Thr Ala Pro Gly Gly Ser Gly Ala Gly Glu
        1055                1060                1065

Glu Arg Met Pro Pro Ser Leu Gln Glu Arg Val Pro Arg Asp Trp
        1070                1075                1080

Asp Pro Gln Pro Leu Gly Pro Pro Thr Pro Gly Val Pro Asp Leu
        1085                1090                1095

Val Asp Phe Gln Pro Pro Pro Glu Leu Val Leu Arg Glu Ala Gly
        1100                1105                1110

Glu Glu Val Pro Asp Ala Gly Pro Arg Glu Gly Val Ser Phe Pro
        1115                1120                1125

Trp Ser Arg Pro Pro Gly Gln Gly Glu Phe Arg Ala Leu Asn Ala
        1130                1135                1140

Arg Leu Pro Leu Asn Thr Asp Ala Tyr Leu Ser Leu Gln Glu Leu
```

|   |   |   |
|---|---|---|
| 1145 | 1150 | 1155 |
| Gln Gly Gln Asp Pro Thr His Leu | | |
| 1160 | 1165 | |